(12) United States Patent
King et al.

(10) Patent No.: US 12,371,355 B2
(45) Date of Patent: Jul. 29, 2025

(54) MICROORGANISMS FOR TREATMENT OF WASTE, WATER, OR SOIL OR FOR FEEDING TO ANIMALS

(71) Applicant: MICROBIAL DISCOVERY GROUP, LLC, Franklin, WI (US)

(72) Inventors: Michael R. King, Oak Creek, WI (US); Sona Son, Cudahy, WI (US); Claire Heile, Franklin, WI (US); Megan Duersteler, Franklin, WI (US)

(73) Assignee: MICROBIAL DISCOVERY GROUP, LLC, Franklin, WI (US)

( * ) Notice: Subject to any disclaimer, the term of this patent is extended or adjusted under 35 U.S.C. 154(b) by 454 days.

(21) Appl. No.: 17/638,223

(22) PCT Filed: Aug. 27, 2020

(86) PCT No.: PCT/US2020/048101
§ 371 (c)(1),
(2) Date: Feb. 25, 2022

(87) PCT Pub. No.: WO2021/041603
PCT Pub. Date: Mar. 4, 2021

(65) Prior Publication Data
US 2022/0289607 A1    Sep. 15, 2022

Related U.S. Application Data

(60) Provisional application No. 63/020,507, filed on May 5, 2020, provisional application No. 62/892,150, filed on Aug. 27, 2019.

(51) Int. Cl.
| | |
|---|---|
| C02F 3/34 | (2023.01) |
| A23K 10/18 | (2016.01) |
| B09B 3/60 | (2022.01) |
| B09C 1/10 | (2006.01) |
| C12N 1/20 | (2006.01) |
| C02F 101/10 | (2006.01) |
| C02F 101/30 | (2006.01) |
| C02F 101/34 | (2006.01) |
| C02F 103/28 | (2006.01) |
| C12R 1/10 | (2006.01) |
| C12R 1/11 | (2006.01) |
| C12R 1/125 | (2006.01) |

(52) U.S. Cl.
CPC ............. *C02F 3/342* (2013.01); *A23K 10/18* (2016.05); *B09B 3/60* (2022.01); *B09C 1/10* (2013.01); *C12N 1/205* (2021.05); *C02F 2101/10* (2013.01); *C02F 2101/308* (2013.01); *C02F 2101/34* (2013.01); *C02F 2103/28* (2013.01); *C02F 2303/02* (2013.01); *C12R 2001/10* (2021.05); *C12R 2001/11* (2021.05); *C12R 2001/125* (2021.05)

(58) Field of Classification Search
CPC . C02F 3/342; C02F 3/34; C12N 1/205; C12R 2001/10; C12R 2001/11; C12R 2001/125; A23K 10/18
See application file for complete search history.

(56) References Cited

U.S. PATENT DOCUMENTS

| | | | |
|---|---|---|---|
| 2008/0050774 A1 | 2/2008 | Berka et al. | |
| 2013/0098037 A1 | 4/2013 | Maier | |
| 2013/0216586 A1 | 8/2013 | Lebrun et al. | |
| 2015/0290254 A1 | 10/2015 | Remus et al. | |
| 2017/0166466 A1* | 6/2017 | King .................. | C02F 3/342 |

FOREIGN PATENT DOCUMENTS

| | | | | |
|---|---|---|---|---|
| CN | 104371939 B | * | 2/2015 | ............... C10N 1/20 |
| CN | 107841478 A | | 3/2018 | |

(Continued)

OTHER PUBLICATIONS

Al-Gheethi AAS. Recycling of sewage sludge as production medium for cellulase by a Bacillus megaterium strain. Int J Recycl Org Waste Agricult. 2015;4:105-119.*

(Continued)

*Primary Examiner* — Lynn Y Fan
(74) *Attorney, Agent, or Firm* — Barnes & Thornburg LLP

(57) ABSTRACT

The invention relates to compositions comprising microbial strains and methods for use of the compositions in removing pollutants in waste, water, or soil, such as remediating dye and lignin, reducing contaminants, degrading paper (such as flushable or disposable or non-flushable wipes), reducing odor, reducing chemical oxygen demand (COD), and combinations thereof, in the water, the soil, or the waste or for use in administration to animals in the feed or drinking water of the animals. More particularly, the invention relates to compositions of isolated *Bacillus* strains selected from the group consisting of isolated *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains, and combinations thereof, and methods for use of these strains for removing pollutants in waste, water, or soil, such as remediating dye and lignin, reducing contaminants, degrading paper (such as flushable or disposable or non-flushable wipes), reducing odor, reducing chemical oxygen demand (COD), and combinations thereof, in the water, the soil, or the waste or for use in administration to animals in the feed or drinking water of the animals.

25 Claims, 9 Drawing Sheets

(56) References Cited

FOREIGN PATENT DOCUMENTS

| | | |
|---|---|---|
| CN | 109497281 A | 3/2019 |
| EP | 1468968 A1 | 10/2004 |
| WO | WO-2014189963 A1 * 11/2014 | ............... C12N 1/20 |
| WO | WO2019/090068 | 5/2019 |
| WO | 2020/072578 A1 | 4/2020 |
| WO | 2023/018686 A1 | 2/2023 |

OTHER PUBLICATIONS

"Bacillus Strains Improving Health and Performance of Production Animals", ED—Darl Kuhn, ip.com, ip.com Inc., West Henrietta, NY, US, (Feb. 11, 2016), XP013170586, ISSN: 1533-0001. (equivalent to U.S. Pat. No. 11,331,351 B2).

Partial supplementary European search report for counterpart EP Application No. 20858946.5, dated Aug. 23, 2023.

PCT Search Report and Written Opinion prepared for PCT Application No. PCT/US2020/048101, completed Dec. 27, 2020.

Sonune, Nilesh, et al., "Isolation, Characterization and Identification of Extracellular Enzyme Producer Bacillus licheniformis from Municipal Wastewater and Evaluation of their Biodegradability," 2018, Biotechnology Research and Innovation, vol. 2, Nr: 1, pp. 37-44.

Safitri, Ratu, et al., "Ability of Bacterial Consortium: *Bacillus coagulans, Bacilus licheniformis, Bacillus pumilus, Bacillus subtilis, Nitrosomonas* Sp. and *Pseudomonas putida* in Bioremediation of Waste Water in Cisirung Waste Water Treatment Plant," 2015, AgroLife Scientific Journal, vol. 4, Nr: 1, pp. 146-152.

* cited by examiner

Strain 1000 - Primer 2 (left) and primer 3 (right)

Strain 1001 - Primer 2 (left) and primer 3 (right)

Strain 8001 - Primer 2 (left) and primer 3 (right)

Strain 1047 - Primer 2 (left) and primer 3 (right)

Strain 1607 - Primer 1, 2, 3, 4, 5, and 6 (left to right)

Strain V18 - Primers 2 (left) and primer 3 (right)

Strain V17 - Primers 2 (left) and primer 3 (right)

Strain 1728 and 2705 - Primers 2 (left) and primer 3 (right)

MICROORGANISMS FOR TREATMENT OF WASTE, WATER, OR SOIL OR FOR FEEDING TO ANIMALS

CROSS-REFERENCE TO RELATED APPLICATIONS

This application is a national stage entry under 35 USC § 371 (b) of PCT International Application No. PCT/US2020/048101, filed Aug. 27, 2020, which claims priority under 35 U.S.C. § 119 (e) to U.S. Provisional Application Ser. No. 62/892,150 filed on Aug. 27, 2019 and U.S. Provisional Application Ser. No. 63/020,507 filed on May 5, 2020 the disclosures of all of which are expressly incorporated by reference herein.

FIELD OF THE DISCLOSURE

The invention relates to compositions comprising microbial strains and methods for use of the compositions in removing pollutants in waste, water, or soil, such as remediating dye and lignin, reducing contaminants, reducing odor, reducing chemical oxygen demand (COD), degrading paper (such as disposable flushable or non-flushable wipes), and combinations thereof, in the water, the soil, or the waste, or for use in administration to animals in the feed or drinking water of the animals. More particularly, the invention relates to compositions of isolated *Bacillus* strains selected from the group consisting of isolated *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), or strains having all of the identifying characteristics of these strains, and combinations thereof, and methods for use of these strains for removing pollutants in waste, water, or soil, such as remediating dye and lignin, reducing contaminants, degrading paper (such as disposable flushable or non-flushable wipes), reducing odor, reducing chemical oxygen demand (COD), and combinations thereof, in the water, the soil, or the waste or for use in administration to animals in the feed or drinking water of the animals.

BACKGROUND AND SUMMARY OF THE INVENTION

Dyes are predominantly synthetic, organic aromatic compounds classified according to their solubility and chemical properties. Commercially, the two most important classes of dyes are azo and anthraquinone dyes, which account for approximately 66% and 15% of all colorants, respectively. Dye classifications are split between two groups indicating application. The first group includes acid, metal-complex, direct, basic and disperse dyes for use on wool, protein fibers, polyamides, cotton, linen, viscose, acrylic, polyesters and/or ethanoates. The second group includes reactive sulfur and vat dyes for use on cotton, linen, viscose, wool and silk. The largest water-soluble dye classes include reactive and direct dyes, accounting for approximately 20-50% and 5-20% of dyes produced respectively. Reactive dyes are often used to color cotton, linen, viscose, wool and silk; direct dyes are used to color cotton, linen and viscose. Commonly manufactured and referenced azo dyes include Reactive Red 120 (R120), Reactive Orange 16 (RO16), Direct Yellow 27 (DY27) and Reactive Black 5 (RB5). Common anthraquinone dyes include Reactive Blue 4 (RB4) and Remazol Brilliant Blue R (RBBR), alternatively called Reactive Blue 19.

The synthesis of industrial dyes is one of the leading causes of water pollution as dyes and pigments are designed to resist biodegradation. During the dying process, an average of 12% of the dye is wasted and 20% of that waste is released to the environment where it can persist for decades (e.g., the half-life of RBBR is approximately forty-six years at 25° C., pH 7.0). Both chemical and structural properties of dyes make them resistant to decay.

Lignin is one of the most abundant organic aromatic polymers in nature as it is a constituent of the cell wall of vascular plants. Lignin is also a byproduct of pulp and paper manufacturing where it persists as waste biomass. Its resistance to degradation and the chemical treatments used to remove lignin from wastewater often lead to acute toxicity, increased light absorption and eutrophication. Discharge generated from the pulping process is considered to be one of the largest pollutants; the pulp and paper industries use an average of 250-500 $m^3$ water per ton of paper produced. Approximately 75% of water used is discharged as effluent and on average contains 50-95 mg/L lignin.

Quantifying the byproducts of lignin degradation is difficult as they subsist as trace amounts in hydrolysates. Traditional methods of studying degradation involve the observation of phenylpropanoid lignol monomers (methoxylated to various degrees). Due to the similar structure of anthraquionic dyes and the comparable breakdown of complex aromatic structures, anthraquinone dye can be used as an indicator of ligninolitic activity. For example, the decolorization of RBBR dye can be used to indirectly estimate ligninolitic activity. Another method involves the use of 10-Acetyl-3,7 dihydroxyphenoxazine because it produces the flouorescent intermediate resorufin when in the presence of peroxidase and excess hydrogen peroxide. The resorufin can be used to measure peroxidase activity in fluorometric and spectrophotometric quantitative assays. A third method measures laccase activity using Syringaldazine as substrate.

The degradation of paper products and wipes in municipal sewer systems, lift stations, and wastewater treatment plants is also a problem that needs to be addressed. Use of flushable nonwoven disposable wipes, including baby wipes, cosmetic wipes, and wet toilet wipes can cause problems in wastewater treatment systems. The nonwoven wipes, though marketed as flushable and biodegradable, are thicker and stronger than standard toilet paper and take much longer to break down. This can result in ragging, a problem where wipes become tangled and knotted and build up in sewer systems and pumps causing blockages. Additionally, wipes and paper towels not intended to be flushed often make their way into sewer systems. Non-flushable wipes and paper towels often have plastic fibers woven into them which makes them even more difficult to degrade than flushable wipes. Accumulation of other organic solids and fats, oils, and grease combine with accumulated wipes and contribute to blockages. Wipes often need to be physically removed from sewer systems or untangled from pumps and other equipment to prevent sewer backups and damage to equipment. Removal can be both labor intensive and costly. Bioaugmentation with bacteria and enzymes has the potential to speed up degradation of paper and wipes in sewer systems, reducing ragging and the need for physical removal and equipment maintenance. Flushable wipes are mostly made from wood pulp, though they can contain some synthetic materials. Wood pulp is mainly comprised of cellulose, which can be broken down into glucose or polysaccharides by the enzyme cellulase. The accelerated degradation of cellulose by cellulase and cellulase producing bacteria can help prevent ragging by breaking apart nonwoven flushable wipes. Some *Bacillus* strains are able to produce enzymes that degrade polyethylene which can help digest plastic fibers in non-flushable wipes. Additionally, bacteria can digest organic solids such as fats, oil, and grease that contribute to the accumulation of wipes.

The present invention relates to compositions comprising microorganisms for use in remediation of dye or lignin-contaminated or paper or wipe-containing water, soil, or waste and/or for use in methods for reducing contaminants, reducing odor, reducing chemical oxygen demand (COD), and combinations thereof, in water, soil, or waste or for use in administration to animals in the feed or drinking water of the animals.

Applicant has developed *Bacillus* strains, and combinations thereof, that are useful for water, soil and waste treatment, dye and lignin degradation, discoloration of dyes, paper or wipe degradation and controlling the detrimental effects of waste, such as by reducing or removing a pollutant (e.g., aromatic polymers and aromatic compounds and paper-containing pollutants, such as wipes (e.g., disposable and non-flushable wipes)) and/or reducing odor, and/or reducing chemical oxygen demand (COD) or for use in administration to animals in the feed or drinking water of the animals.

For example, these microorganisms (i.e., *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), and/or *Bacillus megaterium* MDG-2705 (NRRL No. B-67619)) accelerate dye and lignin degradation and discoloration and secrete enzymes including, but not limited to, oxidoreductases, hydrolases, transferases, lyases, isomerases, ligases, peroxidases, laccases, esterases, amylases, proteases, xylanases, lipases, cellulases, oxygenases, reductases, oxidases, hydroxylases, and dehydrogenases, capable of improving the quality of industrial wastewater systems and soil and water (e.g., by remediating dye, lignin, and paper-contaminated soil, waste, and water). These *Bacillus* strains can also reduce odors, reduce organics, reduce chemical oxygen demand, and reduce contaminants, including but not limited to, lignin and dyes (e.g., acid, metal-complex, direct, basic, disperse, reactive, sulfur and vat dyes), and the like. In still other embodiments, the *Bacillus* strains can be administered to an animal in animal feed or in the drinking water of the animal and can improve the performance of the animal (e.g., decrease feed conversion, increase average daily feed intake, increase average daily gain, improve consistency of performance, and combinations thereof), improve the health of the animal, improve the environment of the animal, and combinations thereof.

In one embodiment, a method of treating water, soil or waste by contacting the water, the soil or the waste with a *Bacillus* strain to remove a pollutant is provided. The method comprises contacting the water, the soil or the waste with an effective amount of an isolated *Bacillus* strain selected from the group consisting of *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains, and removing the pollutant.

In another embodiment, a commercial package is provided. The commercial package comprises an isolated *Bacillus* strain selected from the group consisting of *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains.

In yet another embodiment, a method of feeding an animal is provided. The method comprises the step of administering to the animal a feed composition or drinking water comprising an effective amount of an additive comprising an isolated *Bacillus* strain selected from the group consisting of *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains, and combinations thereof.

The various embodiments described in the numbered clauses below are applicable to any of the embodiments described in this "SUMMARY" section and the sections of the patent application titled "DETAILED DESCRIPTION OF ILLUSTRATIVE EMBODIMENTS" or "EXAMPLES" or in the "CLAIMS" appended to this application:

1. A method of treating water, soil or waste by contacting the water, the soil or the waste with a *Bacillus* strain to remove a pollutant, the method comprising contacting the water, the soil or the waste with an effective amount of an isolated *Bacillus* strain selected from the group consisting of *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains, and removing the pollutant.

2. The method of clause 1 wherein the water or the waste is treated to remove a pollutant and the water or the waste is selected from the group consisting of industrial wastewater, industrial waste, residential wastewater, residential waste, agricultural wastewater, agricultural waste, and wastewater.

3. The method of clause 1 or 2 wherein removing the pollutant results in a reduction in odor or a reduction in chemical oxygen demand in the water, the waste, or the soil.

4. The method of any one of clauses 1 to 3 wherein the pollutant is an organic compound.

5. The method of clause 4 wherein the organic compound is removed by degradation.

6. The method of any one of clauses 1 to 5 wherein the pollutant is a synthetic compound.

7. The method of any one of clauses 1 to 6 wherein the pollutant is a paper-containing compound.

8. The method of clause 7 wherein the paper-containing compound is a wipe.

9. The method of any one of clauses 1 to 8 wherein at least one of the *Bacillus* strains has antimicrobial activity.

10. The method of clause 9 wherein the antimicrobial activity is against a bacterium selected from the group consisting of an *E. coli* bacterium, a *Salmonella* bacterium, a *Staphylococcus* bacterium, an *Enterococcus* bacterium, a *Campylobacter* bacterium, and combinations thereof.

11. The method of any one of clauses 1 to 10 wherein the *Bacillus* strain produces an enzyme selected from the group consisting of an oxidoreductase, a hydrolase, a transferase, a lyase, an isomerase, a ligase, a peroxidase, a laccase, an esterase, an amylase, a protease, a xylanase, a lipase, a cellulase, an oxygenase, a reductase, an oxidase, a hydroxylase, a dehydrogenase, and combinations thereof.

12. The method of clause 11 wherein the enzyme is an oxidoreductase.

13. The method of clause 11 wherein the enzyme is a hydrolase.

14. The method of clause 11 wherein the enzyme is a transferase.

15. The method of clause 11 wherein the enzyme is a lyase.

16. The method of clause 11 wherein the enzyme is an isomerase.

17. The method of clause 11 wherein the enzyme is a ligase.

18. The method of clause 11 wherein the enzyme is a peroxidase.

19. The method of clause 11 wherein the enzyme is a laccase.

20. The method of clause 11 wherein the enzyme is an esterase.

21. The method of clause 11 wherein the enzyme is an amylase.

22. The method of clause 11 wherein the enzyme is a protease.

23. The method of clause 11 wherein the enzyme is a xylanase.

24. The method of clause 11 wherein the enzyme is a lipase.

25. The method of clause 11 wherein the enzyme is a cellulase.

26. The method of clause 11 wherein the enzyme is an oxygenase.

27. The method of clause 11 wherein the enzyme is a reductase.

28. The method of clause 11 wherein the enzyme is an oxidase.

29. The method of clause 11 wherein the enzyme is a hydroxylase.

30. The method of clause 11 wherein the enzyme is a dehydrogenase.

31. The method of any one of clauses 1 to 30 further comprising treating the water, the soil or the waste with another bacterial strain selected from the group consisting of another *Bacillus* strain, a lactic acid bacterial strain, and combinations thereof.

32. The method of any one of clauses 1 to 31 wherein the effective amount of the *Bacillus* strain is about $1.0 \times 10^2$ CFU/gram of the water, the soil or the waste to about $1.0 \times 10^6$ CFU/gram of the water, the soil or the waste.

33. The method of any one of clauses 1 to 31 wherein the effective amount of the *Bacillus* strain is about $1.0 \times 10^2$ CFU/gram of the water, the soil or the waste to about $1.0 \times 10^4$ CFU/gram of the water, the soil or the waste.

34. The method of any one of clauses 1 to 31 wherein the effective amount is about $1.0 \times 10^2$ CFU/gram of the water, the soil, or the waste to about $1.0 \times 10^3$ CFU/gram of the water, the soil, or the waste.

35. The method of any one of clauses 1 to 34 further comprising contacting the water, the soil, or the waste with an exogenous enzyme selected from the group consisting of an oxidoreductase, a hydrolase, a transferase, a lyase, an isomerase, a ligase, a peroxidase, a laccase, an esterase, an amylase, a protease, a xylanase, a lipase, a cellulase, an oxygenase, a reductase, an oxidase, a hydroxylase, a dehydrogenase, and combinations thereof.

36. The method of any one of clauses 1 to 35 wherein the strain administered is *Bacillus subtilis* MDG-1728 (NRRL No. B-67618) or a strain having all of the identifying characteristics of *Bacillus subtilis* MDG-1728 (NRRL No. B-67618).

37. The method of any one of clauses 1 to 35 wherein the strain administered is *Bacillus* strain *Bacillus megaterium* MDG-2705 (NRRL No. B-67619) or a strain having all of the identifying characteristics of *Bacillus megaterium* MDG-2705 (NRRL No. B-67619).

38. The method of any one of clauses 1 to 35 wherein the strain administered is *Bacillus* strain *Bacillus licheniformis* MDG-1000 (NRRL No. B-67888), or a strain having all of the identifying characteristics of *Bacillus licheniformis* MDG-1000 (NRRL No. B-67888).

39. The method of any one of clauses 1 to 35 wherein the strain administered is *Bacillus* strain *Bacillus amyloliquefaciens* MDG1607 (NRRL No. B-67666), or a strain having all of the identifying characteristics of *Bacillus amyloliquefaciens* strain MDG1607 (NRRL No. B-67666).

40. The method of any one of clauses 1 to 35 wherein the strain administered is *Bacillus* strain *Bacillus licheniformis* MDG-1001 (NRRL No. B-67889), or a strain having all of the identifying characteristics of *Bacillus licheniformis* MDG-1001 (NRRL No. B-67889).

41. The method of any one of clauses 1 to 35 wherein the strain administered is *Bacillus* strain *Bacillus subtilis/amyloliquefaciens* MDG-8001 (NRRL No. B-67890), or a strain having all of the identifying characteristics of *Bacillus subtilis/amyloliquefaciens* MDG-8001 (NRRL No. B-67890).

42. The method of any one of clauses 1 to 35 wherein the strain administered is *Bacillus* strain *Bacillus pumilus* MDG-1047 (NRRL No. B-67891), or a strain having all of the identifying characteristics of *Bacillus pumilus* MDG-1047 (NRRL No. B-67891).

43. The method of any one of clauses 1 to 35 wherein the strain administered is *Bacillus* strain *Bacillus subtilis*

MDGV18 (NRRL No. B-67665), or a strain having all of the identifying characteristics of *Bacillus subtilis* MDGV18 (NRRL No. B-67665).

44. The method of any one of clauses 1 to 35 wherein the strain administered is *Bacillus* strain *Bacillus pumilus* MDGV17 (NRRL No. B-67664) or a strain having all of the identifying characteristics of *Bacillus pumilus* MDGV17 (NRRL No. B-67664).

45. The method of any one of clauses 1 to 35 wherein the strain administered is *Bacillus subtilis* MDG-1728 (NRRL No. B-67618).

46. The method of any one of clauses 1 to 35 wherein the strain administered is *Bacillus* strain *Bacillus megaterium* MDG-2705 (NRRL No. B-67619).

47. The method of any one of clauses 1 to 35 wherein the strain administered is *Bacillus* strain *Bacillus licheniformis* MDG-1000 (NRRL No. B-67888).

48. The method of any one of clauses 1 to 35 wherein the strain administered is *Bacillus* strain *Bacillus amyloliquefaciens* MDG1607 (NRRL No. B-67666).

49. The method of any one of clauses 1 to 35 wherein the strain administered is *Bacillus* strain *Bacillus licheniformis* MDG-1001 (NRRL No. B-67889).

50. The method of any one of clauses 1 to 35 wherein the strain administered is *Bacillus* strain *Bacillus subtilis/amyloliquefaciens* MDG-8001 (NRRL No. B-67890).

51. The method of any one of clauses 1 to 35 wherein the strain administered is *Bacillus* strain *Bacillus pumilus* MDG-1047 (NRRL No. B-67891).

52. The method of any one of clauses 1 to 35 wherein the strain administered is *Bacillus* strain *Bacillus subtilis* MDGV18 (NRRL No. B-67665).

53. The method of any one of clauses 1 to 35 wherein the strain administered is *Bacillus* strain *Bacillus pumilus* MDGV17 (NRRL No. B-67664).

54. The method of any one of clauses 1 to 6 or 9 to 35 wherein the pollutant is a dye.

55. The method of clause 54 wherein the dye is an azo dye or an anthraquinone dye.

56. The method of clause 54 or 55 wherein the pollutant is an acid dye.

57. The method of clause 54 or 55 wherein the pollutant is a metal-complex dye.

58. The method of clause 54 or 55 wherein the pollutant is a direct dye.

59. The method of clause 54 or 55 wherein the pollutant is a basic dye.

60. The method of clause 54 or 55 wherein the pollutant is a disperse dye.

61. The method of clause 54 or 55 wherein the pollutant is a reactive dye.

62. The method of clause 54 or 55 wherein the pollutant is a sulfur dye.

63. The method of clause 54 or 55 wherein the pollutant is a vat dye.

64. The method of any one of clauses 54 to 63 wherein the pollutant is a dye and the *Bacillus* strain causes degradation or discoloration of the dye.

65. The method of any one of clauses 1 to 53 wherein the pollutant is a lignin.

66. The method of clause 65 wherein the lignin is produced by the paper industry or the pulp industry.

67. The method of any one of clauses 1 to 3 or 6 to 53 wherein the pollutant is an inorganic compound.

68. A commercial package comprising an isolated *Bacillus* strain selected from the group consisting of *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus subtilis* MDGV18 (NRRL No. B-67665), *Bacillus subtilis* MDG-1728 (NRRL No. B-67618), *Bacillus megaterium* MDG-2705 (NRRL No. B-67619), and strains having all of the identifying characteristics of these strains.

69. The commercial package of clause 68 wherein the *Bacillus* strain causes an effect selected from the group consisting of a reduction in odor, a reduction in chemical oxygen demand, a degradation of a dye, a discoloration of a dye, a degradation of a lignin, and a combination thereof in water, waste, or soil.

70. The commercial package of clause 68 or 69 wherein the *Bacillus* strain is in the form of a concentrate.

71. The commercial package of clause 68 or 69 wherein the *Bacillus* strain is in the form of a super concentrate.

72. The commercial package of any one of clauses 68 to 71 wherein the *Bacillus* strain is in dry form.

73. The commercial package of any one of clauses 68 to 72 wherein the *Bacillus* strain is in pelleted form.

74. The commercial package of any one of clauses 68 to 71 wherein the *Bacillus* strain is in a liquid form.

75. The commercial package of any one of clauses 68 to 74 further comprising a carrier for the *Bacillus* strain.

76. The commercial package of any one of clauses 68 to 75 wherein the commercial package comprises a bag.

77. The commercial package of clause 76 wherein the bag is a plastic bag.

78. The commercial package of any one of clauses 68 to 77 further comprising instructions for use of one or more of the *Bacillus* strains.

79. The commercial package of any one of clauses 68 to 78 comprising a 20-pound bag.

80. The commercial package of any one of clauses 68 to 78 comprising a 50-pound bag.

81. The commercial package of any one of clauses 68 to 72 or 75 to 80 in powder form.

82. The commercial package of any one of clauses 68 to 81 comprising a container for commercial use wherein the container comprises plastic.

83. The commercial package of any one of clauses 68 to 81 comprising a container for commercial use wherein the container comprises paper.

84. The commercial package of any one of clauses 68 to 83 further comprising a binder.

85. The commercial package of clause 84 wherein the binder is selected from the group consisting of clay, yeast cell wall components, aluminum silicate, and glucan, or combinations thereof.

86. The commercial package of any one of clauses 68 to 85 wherein the *Bacillus* strain causes an effect selected from the group consisting of a degradation of a dye, a discoloration of a dye, a degradation of a lignin, and a combination thereof in water, waste, or soil.

87. The commercial package of any one of clauses 68 to 86 wherein the *Bacillus* strain causes a discoloration of a dye or a degradation of a dye in waste, water, or soil.

88. The commercial package of any one of clauses 68 to 86 wherein the *Bacillus* strain causes a degradation of a lignin in water, waste, or soil.

89. A method of feeding an animal, comprising the step of administering to the animal a feed composition or drinking water comprising an effective amount of an additive comprising an isolated *Bacillus* strain selected from the group consisting of *Bacillus* strains *Bacillus licheniformis* MDG- 1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains, and combinations thereof.

90. The method of clause 89 wherein the animal is selected from the group consisting of a poultry species, a porcine species, a caprine species, a bovine species, an ovine species, and an equine species.

91. The method of clause 90 wherein the animal is a porcine species and the porcine species is selected from the group consisting of a grow finish pig, a nursery pig, a sow, and a breeding stock pig.

92. The method of any one of clauses 89 to 91 wherein the *Bacillus* strain produces an enzyme selected from the group consisting of an α-galactosidase, a protease, a lipase, an amylase, a xylanase, a cellulase, and combinations thereof.

93. The method of any one of clauses 89 to 92 further comprising the step of administering to the animal another bacterial strain selected from the group consisting of another *Bacillus* strain, a lactic acid bacterial strain, and combinations thereof.

94. The method of any one of clauses 89 to 93 wherein the strain administered is *Bacillus subtilis* MDG-1728 (NRRL No. B-67618).

95. The method of any one of clauses 89 to 93 wherein the strain administered is *Bacillus* strain *Bacillus megaterium* MDG-2705 (NRRL No. B-67619).

96. The method of any one of clauses 89 to 93 wherein the strain administered is *Bacillus* strain *Bacillus licheniformis* MDG-1000 (NRRL No. B-67888).

97. The method of any one of clauses 89 to 93 wherein the strain administered is *Bacillus* strain *Bacillus amyloliquefaciens* MDG1607 (NRRL No. B-67666).

98. The method of any one of clauses 89 to 93 wherein the strain administered is *Bacillus* strain *Bacillus licheniformis* MDG-1001 (NRRL No. B-67889).

99. The method of any one of clauses 89 to 93 wherein the strain administered is *Bacillus* strain *Bacillus subtilis/amyloliquefaciens* MDG-8001 (NRRL No. B-67890).

100. The method of any one of clauses 89 to 93 wherein the strain administered is *Bacillus* strain *Bacillus pumilus* MDG-1047 (NRRL No. B-67891).

101. The method of any one of clauses 89 to 93 wherein the strain administered is *Bacillus* strain *Bacillus subtilis* MDGV18 (NRRL No. B-67665).

102. The method of any one of clauses 89 to 93 wherein the strain administered is *Bacillus* strain *Bacillus pumilus* MDGV17 (NRRL No. B-67664).

103. The method of any one of clauses 89 to 102 wherein the *Bacillus* strain is administered in the feed composition at a dose of about $1.0 \times 10^3$ CFU/gram of the feed composition to about $5.0 \times 10^{12}$ CFU/gram of the feed composition.

104. The method of any one of clauses 89 to 102 wherein the *Bacillus* strain is administered in the feed composition at a dose of about $1.0 \times 10^3$ CFU/gram of the feed composition to about $1.0 \times 10^7$ CFU/gram of the feed composition.

105. The method of any one of clauses 89 to 102 wherein the *Bacillus* strain is administered in the feed composition at a dose greater than about $7.0 \times 10^4$ CFU/gram of the feed composition.

106. The method of any one of clauses 89 to 102 further comprising the step of administering to the animal an enzyme selected from the group consisting of a galactosidase, a protease, a lipase, an amylase, a hemicellulase, an arabinoxylanases, a xylanase, a cellulase, an NSPase, a phytase, and combinations thereof.

107. The method of clause 91 wherein the animal is a sow and the *Bacillus* strain is administered during lactation.

108. The method of clause 91 wherein the animal is a sow and the *Bacillus* strain is administered during gestation.

109. The method of any one of clauses 89 to 108 wherein the feed composition is administered daily to the animal.

110. The method of clause 89 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

111. The method of clause 35 wherein the enzyme is a cellulase.

112. The method of clause 35 wherein the enzyme is a xylanase.

113. The method of clause 35 wherein the enzyme is a cellulase.

114. The method of clause 35 wherein the enzyme is a xylanase.

115. The commercial package of any one of clauses 68 to 88 further comprising a cellulase.

116. The commercial package of any one of clauses 68 to 88 further comprising a xylanase.

DETAILED DESCRIPTION OF ILLUSTRATIVE EMBODIMENTS

Figure 1A:
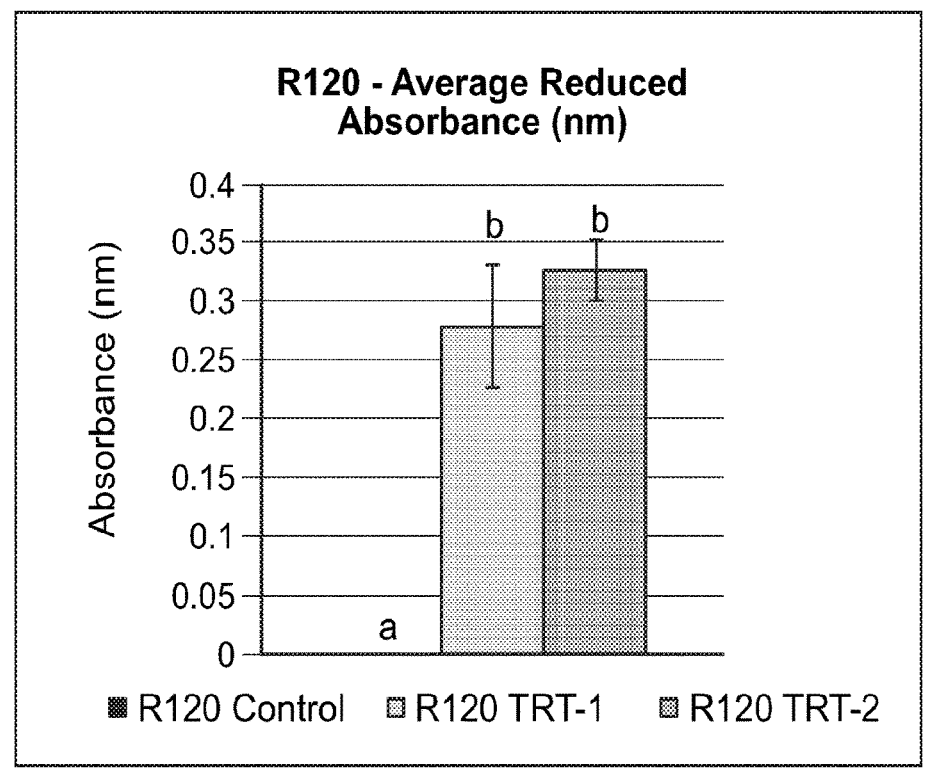
FIG. 1A is a graph showing bioremediation results of colorant R120.
Figure 1B:
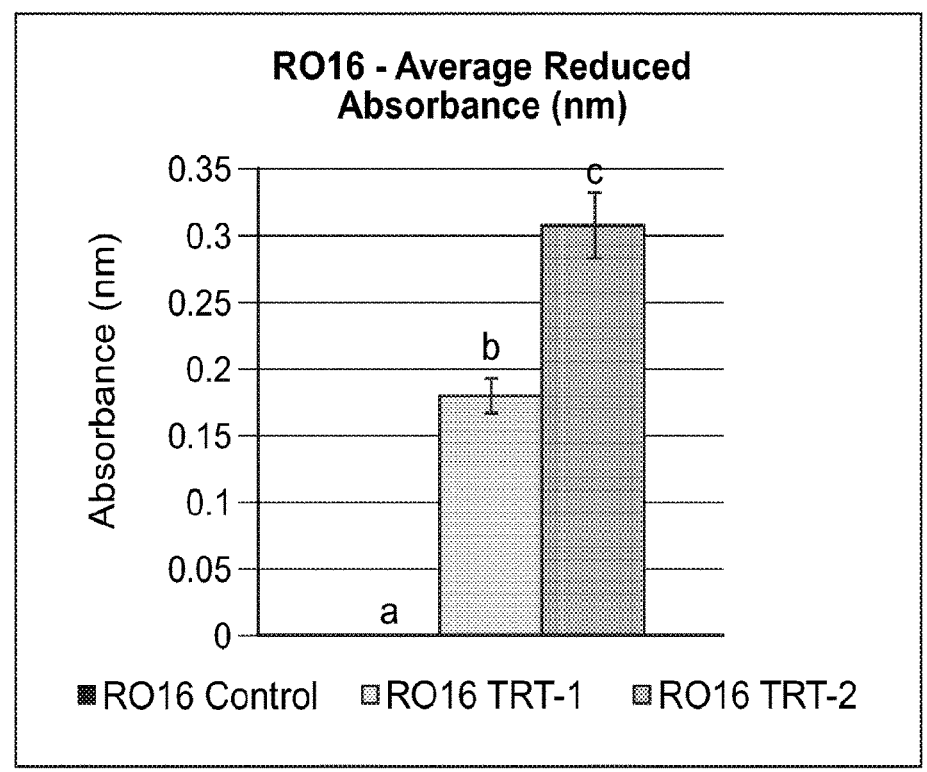
FIG. 1B is a graph showing bioremediation results of colorant RO16.
Figure 1C:
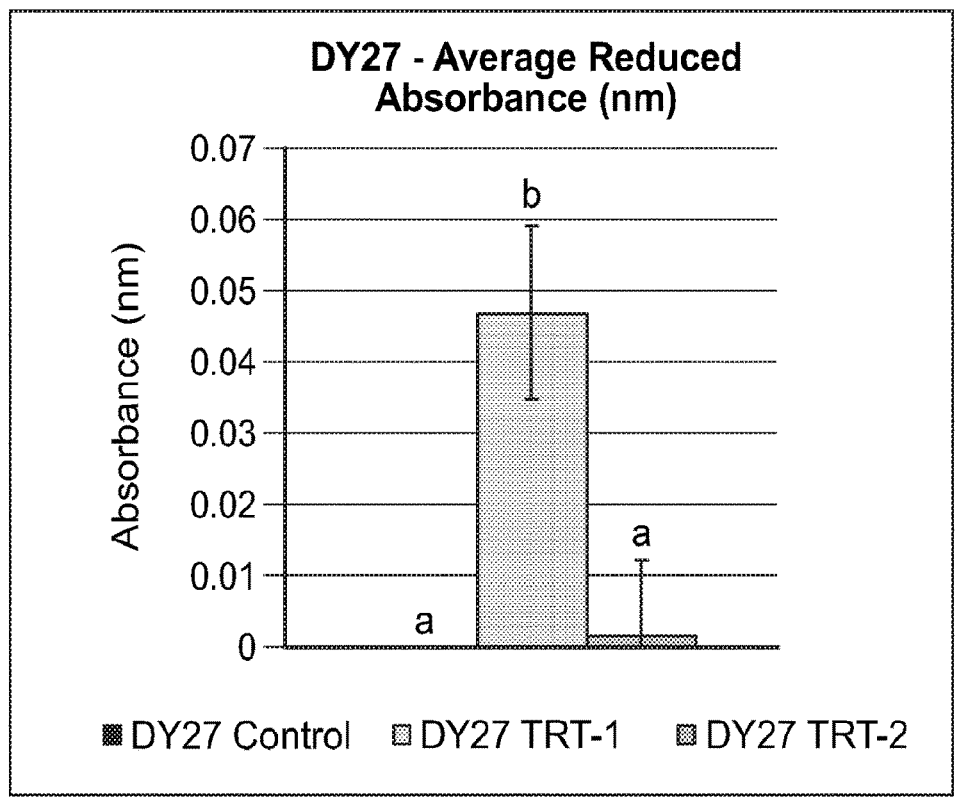
FIG. 1C is a graph showing bioremediation results of colorant DY27.
Figure 1D:
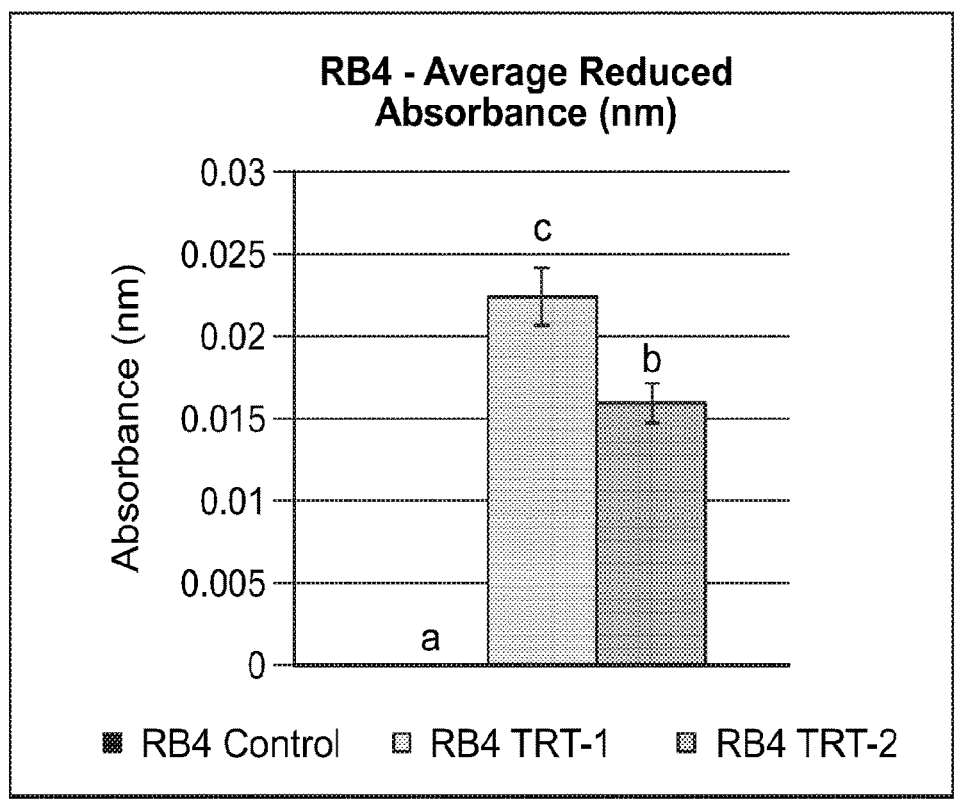
FIG. 1D is a graph showing bioremediation results of colorant RB4.
Figure 1E:
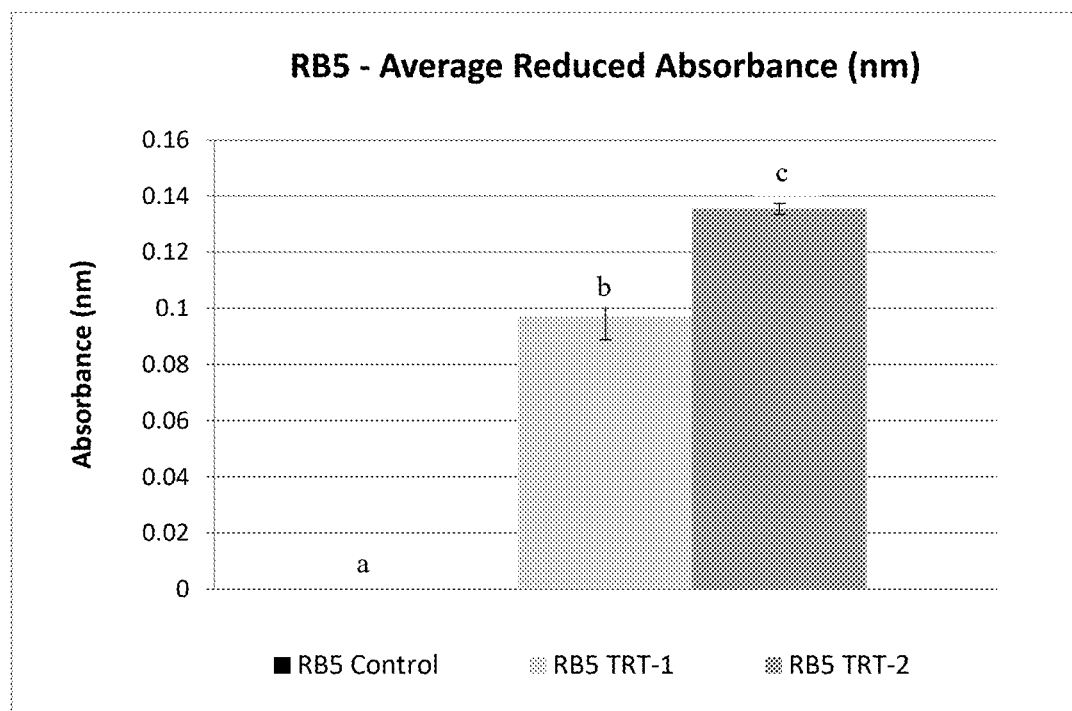
FIG. 1E is a graph showing bioremediation results of colorant RB5.
Figure 1F:
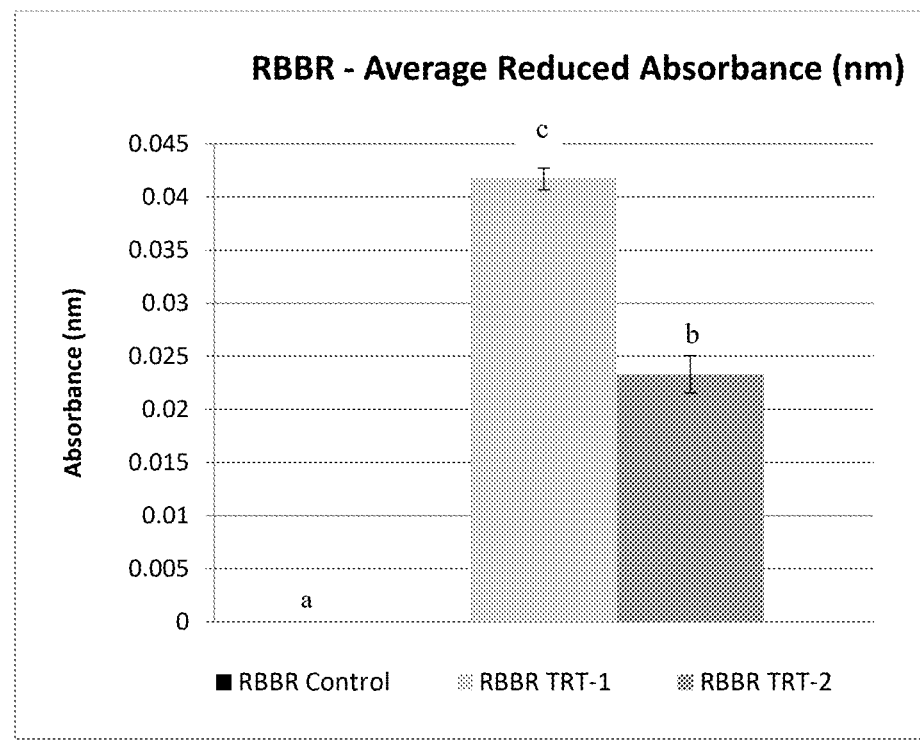
FIG. 1F is a graph showing bioremediation results of colorant RBBR.

The invention relates to compositions comprising microbial strains and methods for use of the compositions in removing pollutants in waste, water, or soil, such as remediating dye and lignin, reducing contaminants, reducing odor, reducing chemical oxygen demand (COD), degrading paper, such as wipes (e.g., flushable and non-flushable wipes), and combinations thereof, in the water, the soil, or the waste or for use in administration to animals in the feed or drinking water of the animals. More particularly, the invention relates to compositions of isolated *Bacillus* strains selected from the group consisting of isolated *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains, and combinations thereof, and methods for use of these strains for removing pollutants in waste, water, or soil, such as remediating dye and lignin, reducing contaminants, degrading paper, such as wipes (e.g., flushable and non-flushable wipes), reducing odor, reducing chemical oxygen demand (COD), and combinations thereof, in the water, the soil, or the waste or for use in administration to animals in the feed or drinking water of the animals.

The various embodiments described in the numbered clauses below are applicable to any of the embodiments described in this "DETAILED DESCRIPTION OF ILLUSTRATIVE EMBODIMENTS" section and the sections of the patent application titled "SUMMARY" or "EXAMPLES" or in the "CLAIMS" appended to this application:

1. A method of treating water, soil or waste by contacting the water, the soil or the waste with a *Bacillus* strain to remove a pollutant, the method comprising contacting the water, the soil or the waste with an effective amount of an isolated *Bacillus* strain selected from the group consisting of *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains, and removing the pollutant.

2. The method of clause 1 wherein the water or the waste is treated to remove a pollutant and the water or the waste is selected from the group consisting of industrial wastewater, industrial waste, residential wastewater, residential waste, agricultural wastewater, agricultural waste, and wastewater.

3. The method of clause 1 or 2 wherein removing the pollutant results in a reduction in odor or a reduction in chemical oxygen demand in the water, the waste, or the soil.

4. The method of any one of clauses 1 to 3 wherein the pollutant is an organic compound.

5. The method of clause 4 wherein the organic compound is removed by degradation.

6. The method of any one of clauses 1 to 5 wherein the pollutant is a synthetic compound.

7. The method of any one of clauses 1 to 6 wherein the pollutant is a paper-containing compound.

8. The method of clause 7 wherein the paper-containing compound is a wipe.

9. The method of any one of clauses 1 to 8 wherein at least one of the *Bacillus* strains has antimicrobial activity.

10. The method of clause 9 wherein the antimicrobial activity is against a bacterium selected from the group consisting of an *E. coli* bacterium, a *Salmonella* bacterium, a *Staphylococcus* bacterium, an *Enterococcus* bacterium, a *Campylobacter* bacterium, and combinations thereof.

11. The method of any one of clauses 1 to 10 wherein the *Bacillus* strain produces an enzyme selected from the group consisting of an oxidoreductase, a hydrolase, a transferase, a lyase, an isomerase, a ligase, a peroxidase, a laccase, an esterase, an amylase, a protease, a xylanase, a lipase, a cellulase, an oxygenase, a reductase, an oxidase, a hydroxylase, a dehydrogenase, and combinations thereof.

12. The method of clause 11 wherein the enzyme is an oxidoreductase.

13. The method of clause 11 wherein the enzyme is a hydrolase.

14. The method of clause 11 wherein the enzyme is a transferase.

15. The method of clause 11 wherein the enzyme is a lyase.

16. The method of clause 11 wherein the enzyme is an isomerase.

17. The method of clause 11 wherein the enzyme is a ligase.

18. The method of clause 11 wherein the enzyme is a peroxidase.

19. The method of clause 11 wherein the enzyme is a laccase.

20. The method of clause 11 wherein the enzyme is an esterase.

21. The method of clause 11 wherein the enzyme is an amylase.

22. The method of clause 11 wherein the enzyme is a protease.

23. The method of clause 11 wherein the enzyme is a xylanase.

24. The method of clause 11 wherein the enzyme is a lipase.

25. The method of clause 11 wherein the enzyme is a cellulase.

26. The method of clause 11 wherein the enzyme is an oxygenase.

27. The method of clause 11 wherein the enzyme is a reductase.

28. The method of clause 11 wherein the enzyme is an oxidase.

29. The method of clause 11 wherein the enzyme is a hydroxylase.

30. The method of clause 11 wherein the enzyme is a dehydrogenase.

31. The method of any one of clauses 1 to 30 further comprising treating the water, the soil or the waste with another bacterial strain selected from the group consisting of another *Bacillus* strain, a lactic acid bacterial strain, and combinations thereof.

32. The method of any one of clauses 1 to 31 wherein the effective amount of the *Bacillus* strain is about $1.0\times10^2$ CFU/gram of the water, the soil or the waste to about $1.0\times10^6$ CFU/gram of the water, the soil or the waste.

33. The method of any one of clauses 1 to 31 wherein the effective amount of the *Bacillus* strain is about $1.0\times10^2$ CFU/gram of the water, the soil or the waste to about $1.0\times10^4$ CFU/gram of the water, the soil or the waste.

34. The method of any one of clauses 1 to 31 wherein the effective amount is about $1.0\times10^2$ CFU/gram of the water, the soil, or the waste to about $1.0\times10^3$ CFU/gram of the water, the soil, or the waste.

35. The method of any one of clauses 1 to 34 further comprising contacting the water, the soil, or the waste with an exogenous enzyme selected from the group consisting of an oxidoreductase, a hydrolase, a transferase, a lyase, an isomerase, a ligase, a peroxidase, a laccase, an esterase, an amylase, a protease, a xylanase, a lipase, a cellulase, an oxygenase, a reductase, an oxidase, a hydroxylase, a dehydrogenase, and combinations thereof.

36. The method of any one of clauses 1 to 35 wherein the strain administered is *Bacillus subtilis* MDG-1728 (NRRL No. B-67618) or a strain having all of the identifying characteristics of *Bacillus subtilis* MDG-1728 (NRRL No. B-67618).

37. The method of any one of clauses 1 to 35 wherein the strain administered is *Bacillus* strain *Bacillus megaterium* MDG-2705 (NRRL No. B-67619) or a strain having all of the identifying characteristics of *Bacillus megaterium* MDG-2705 (NRRL No. B-67619).

38. The method of any one of clauses 1 to 35 wherein the strain administered is *Bacillus* strain *Bacillus licheniformis* MDG-1000 (NRRL No. B-67888), or a strain having all of the identifying characteristics of *Bacillus licheniformis* MDG-1000 (NRRL No. B-67888).

39. The method of any one of clauses 1 to 35 wherein the strain administered is *Bacillus* strain *Bacillus amyloliquefaciens* MDG1607 (NRRL No. B-67666), or a strain having all of the identifying characteristics of *Bacillus amyloliquefaciens* strain MDG1607 (NRRL No. B-67666).

40. The method of any one of clauses 1 to 35 wherein the strain administered is *Bacillus* strain *Bacillus licheniformis* MDG-1001 (NRRL No. B-67889), or a strain having all of the identifying characteristics of *Bacillus licheniformis* MDG-1001 (NRRL No. B-67889).

41. The method of any one of clauses 1 to 35 wherein the strain administered is *Bacillus* strain *Bacillus subtilis/amyloliquefaciens* MDG-8001 (NRRL No. B-67890), or a strain having all of the identifying characteristics of *Bacillus subtilis/amyloliquefaciens* MDG-8001 (NRRL No. B-67890).

42. The method of any one of clauses 1 to 35 wherein the strain administered is *Bacillus* strain *Bacillus pumilus* MDG-1047 (NRRL No. B-67891), or a strain having all of the identifying characteristics of *Bacillus pumilus* MDG-1047 (NRRL No. B-67891).

43. The method of any one of clauses 1 to 35 wherein the strain administered is *Bacillus* strain *Bacillus subtilis* MDGV18 (NRRL No. B-67665), or a strain having all of the identifying characteristics of *Bacillus subtilis* MDGV18 (NRRL No. B-67665).

44. The method of any one of clauses 1 to 35 wherein the strain administered is *Bacillus* strain *Bacillus pumilus* MDGV17 (NRRL No. B-67664) or a strain having all of the identifying characteristics of *Bacillus pumilus* MDGV17 (NRRL No. B-67664).

45. The method of any one of clauses 1 to 35 wherein the strain administered is *Bacillus subtilis* MDG-1728 (NRRL No. B-67618).

46. The method of any one of clauses 1 to 35 wherein the strain administered is *Bacillus* strain *Bacillus megaterium* MDG-2705 (NRRL No. B-67619).

47. The method of any one of clauses 1 to 35 wherein the strain administered is *Bacillus* strain *Bacillus licheniformis* MDG-1000 (NRRL No. B-67888).

48. The method of any one of clauses 1 to 35 wherein the strain administered is *Bacillus* strain *Bacillus amyloliquefaciens* MDG1607 (NRRL No. B-67666).

49. The method of any one of clauses 1 to 35 wherein the strain administered is *Bacillus* strain *Bacillus licheniformis* MDG-1001 (NRRL No. B-67889).

50. The method of any one of clauses 1 to 35 wherein the strain administered is *Bacillus* strain *Bacillus subtilis/amyloliquefaciens* MDG-8001 (NRRL No. B-67890).

51. The method of any one of clauses 1 to 35 wherein the strain administered is *Bacillus* strain *Bacillus pumilus* MDG-1047 (NRRL No. B-67891).

52. The method of any one of clauses 1 to 35 wherein the strain administered is *Bacillus* strain *Bacillus subtilis* MDGV18 (NRRL No. B-67665).

53. The method of any one of clauses 1 to 35 wherein the strain administered is *Bacillus* strain *Bacillus pumilus* MDGV17 (NRRL No. B-67664).

54. The method of any one of clauses 1 to 6 or 9 to 35 wherein the pollutant is a dye.

55. The method of clause 54 wherein the dye is an azo dye or an anthraquinone dye.

56. The method of clause 54 or 55 wherein the pollutant is an acid dye.

57. The method of clause 54 or 55 wherein the pollutant is a metal-complex dye.

58. The method of clause 54 or 55 wherein the pollutant is a direct dye.

59. The method of clause 54 or 55 wherein the pollutant is a basic dye.

60. The method of clause 54 or 55 wherein the pollutant is a disperse dye.

61. The method of clause 54 or 55 wherein the pollutant is a reactive dye.

62. The method of clause 54 or 55 wherein the pollutant is a sulfur dye.

63. The method of clause 54 or 55 wherein the pollutant is a vat dye.

64. The method of any one of clauses 54 to 63 wherein the pollutant is a dye and the *Bacillus* strain causes degradation or discoloration of the dye.

65. The method of any one of clauses 1 to 53 wherein the pollutant is a lignin.

66. The method of clause 65 wherein the lignin is produced by the paper industry or the pulp industry.

67. The method of any one of clauses 1 to 3 or 6 to 53 wherein the pollutant is an inorganic compound.

68. A commercial package comprising an isolated *Bacillus* strain selected from the group consisting of *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus subtilis* MDGV18 (NRRL No. B-67665), *Bacillus subtilis* MDG-1728 (NRRL No. B-67618), *Bacillus megaterium* MDG-2705 (NRRL No. B-67619), and strains having all of the identifying characteristics of these strains.

69. The commercial package of clause 68 wherein the *Bacillus* strain causes an effect selected from the group consisting of a reduction in odor, a reduction in chemical oxygen demand, a degradation of a dye, a discoloration of a dye, a degradation of a lignin, and a combination thereof in water, waste, or soil.

70. The commercial package of clause 68 or 69 wherein the *Bacillus* strain is in the form of a concentrate.

71. The commercial package of clause 68 or 69 wherein the *Bacillus* strain is in the form of a super concentrate.

72. The commercial package of any one of clauses 68 to 71 wherein the *Bacillus* strain is in dry form.

73. The commercial package of any one of clauses 68 to 72 wherein the *Bacillus* strain is in pelleted form.

74. The commercial package of any one of clauses 68 to 71 wherein the *Bacillus* strain is in a liquid form.

75. The commercial package of any one of clauses 68 to 74 further comprising a carrier for the *Bacillus* strain.

76. The commercial package of any one of clauses 68 to 75 wherein the commercial package comprises a bag.

77. The commercial package of clause 76 wherein the bag is a plastic bag.

78. The commercial package of any one of clauses 68 to 77 further comprising instructions for use of one or more of the *Bacillus* strains.

79. The commercial package of any one of clauses 68 to 78 comprising a 20-pound bag.

80. The commercial package of any one of clauses 68 to 78 comprising a 50-pound bag.

81. The commercial package of any one of clauses 68 to 72 or 75 to 80 in powder form.

82. The commercial package of any one of clauses 68 to 81 comprising a container for commercial use wherein the container comprises plastic.

83. The commercial package of any one of clauses 68 to 81 comprising a container for commercial use wherein the container comprises paper.

84. The commercial package of any one of clauses 68 to 83 further comprising a binder.

85. The commercial package of clause 84 wherein the binder is selected from the group consisting of clay, yeast cell wall components, aluminum silicate, and glucan, or combinations thereof.

86. The commercial package of any one of clauses 68 to 85 wherein the *Bacillus* strain causes an effect selected from the group consisting of a degradation of a dye, a discoloration of a dye, a degradation of a lignin, and a combination thereof in water, waste, or soil.

87. The commercial package of any one of clauses 68 to 86 wherein the *Bacillus* strain causes a discoloration of a dye or a degradation of a dye in waste, water, or soil.

88. The commercial package of any one of clauses 68 to 86 wherein the *Bacillus* strain causes a degradation of a lignin in water, waste, or soil.

89. A method of feeding an animal, comprising the step of administering to the animal a feed composition or drinking water comprising an effective amount of an additive comprising an isolated *Bacillus* strain selected from the group consisting of *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains, and combinations thereof.

90. The method of clause 89 wherein the animal is selected from the group consisting of a poultry species, a porcine species, a caprine species, a bovine species, an ovine species, and an equine species.

91. The method of clause 90 wherein the animal is a porcine species and the porcine species is selected from the group consisting of a grow finish pig, a nursery pig, a sow, and a breeding stock pig.

92. The method of any one of clauses 89 to 91 wherein the *Bacillus* strain produces an enzyme selected from the group consisting of an α-galactosidase, a protease, a lipase, an amylase, a xylanase, a cellulase, and combinations thereof.

93. The method of any one of clauses 89 to 92 further comprising the step of administering to the animal another bacterial strain selected from the group consisting of another *Bacillus* strain, a lactic acid bacterial strain, and combinations thereof.

94. The method of any one of clauses 89 to 93 wherein the strain administered is *Bacillus subtilis* MDG-1728 (NRRL No. B-67618).

95. The method of any one of clauses 89 to 93 wherein the strain administered is *Bacillus* strain *Bacillus megaterium* MDG-2705 (NRRL No. B-67619).

96. The method of any one of clauses 89 to 93 wherein the strain administered is *Bacillus* strain *Bacillus licheniformis* MDG-1000 (NRRL No. B-67888).

97. The method of any one of clauses 89 to 93 wherein the strain administered is *Bacillus* strain *Bacillus amyloliquefaciens* MDG1607 (NRRL No. B-67666).

98. The method of any one of clauses 89 to 93 wherein the strain administered is *Bacillus* strain *Bacillus licheniformis* MDG-1001 (NRRL No. B-67889).

99. The method of any one of clauses 89 to 93 wherein the strain administered is *Bacillus* strain *Bacillus subtilis/amyloliquefaciens* MDG-8001 (NRRL No. B-67890).

100. The method of any one of clauses 89 to 93 wherein the strain administered is *Bacillus* strain *Bacillus pumilus* MDG-1047 (NRRL No. B-67891).

101. The method of any one of clauses 89 to 93 wherein the strain administered is *Bacillus* strain *Bacillus subtilis* MDGV18 (NRRL No. B-67665).

102. The method of any one of clauses 89 to 93 wherein the strain administered is *Bacillus* strain *Bacillus pumilus* MDGV17 (NRRL No. B-67664).

103. The method of any one of clauses 89 to 102 wherein the *Bacillus* strain is administered in the feed composition at a dose of about $1.0 \times 10^3$ CFU/gram of the feed composition to about $5.0 \times 10^{12}$ CFU/gram of the feed composition.

104. The method of any one of clauses 89 to 102 wherein the *Bacillus* strain is administered in the feed composition at a dose of about $1.0 \times 10^3$ CFU/gram of the feed composition to about $1.0 \times 10^7$ CFU/gram of the feed composition.

105. The method of any one of clauses 89 to 102 wherein the *Bacillus* strain is administered in the feed composition at a dose greater than about $7.0 \times 10^4$ CFU/gram of the feed composition.

106. The method of any one of clauses 89 to 102 further comprising the step of administering to the animal an enzyme selected from the group consisting of a galactosidase, a protease, a lipase, an amylase, a hemicellulase, an arabinoxylanases, a xylanase, a cellulase, an NSPase, a phytase, and combinations thereof.

107. The method of clause 91 wherein the animal is a sow and the *Bacillus* strain is administered during lactation.

108. The method of clause 91 wherein the animal is a sow and the *Bacillus* strain is administered during gestation.

109. The method of any one of clauses 89 to 108 wherein the feed composition is administered daily to the animal.

110. The method of clause 89 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

111. The method of clause 35 wherein the enzyme is a cellulase.

112. The method of clause 35 wherein the enzyme is a xylanase.

113. The method of clause 35 wherein the enzyme is a cellulase.

114. The method of clause 35 wherein the enzyme is a xylanase.

115. The commercial package of any one of clauses 68 to 88 further comprising a cellulase.

116. The commercial package of any one of clauses 68 to 88 further comprising a xylanase.

In various water, waste, or soil treatment embodiments, the water, the waste, or the soil that is treated to remove a pollutant using the *Bacillus* strains described herein can be selected from the group consisting of industrial wastewater, industrial waste, agricultural wastewater, agricultural waste, wastewater, residential waste, residential wastewater, municipal solid waste, landfill waste, soil waste, composting waste, contaminated groundwater, and leachate from waste. In another embodiment, the strains may be used as a litter treatment.

In various embodiments of the water, waste, or soil treatment methods described herein, the *Bacillus* strain (e.g., *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), or a strain having all of the identifying characteristics of these strains) can have an effect, including but not limited to, effects selected from the group consisting of removal of a pollutant, a reduction in odor, a reduction in chemical oxygen demand, remediation of waste, water, or soil, a degradation of a dye, a discoloration of a dye, a degradation of a lignin, degradation of paper, such as wipes (e.g., flushable and non-flushable wipes), and a combination thereof in water, waste, or soil.

In any water, waste, or soil treatment embodiments described herein, the *Bacillus* strains can be added to waste, water, or soil alone or in any combination, or can be in the form of any composition described herein so that the strains are alone or in any combination in the compositions described herein. The *Bacillus* strains described herein can also be used in combination with other microbial strains, including other *Bacillus* strains or *Lactobacillus* strains. In another embodiment, the additional *Bacillus* strain can be selected from the group consisting of *Bacillus subtilis*, *Bacillus amyloliquefaciens*, *Bacillus licheniformis*, *Bacillus pumilus*, *Bacillus mojavensis*, *Bacillus methylotrophicus*, other *Bacillus* strains, and combinations thereof.

In one embodiment of the invention, an effective amount of the *Bacillus* strain can be added to waste, water, or soil to cause an effect, including but not limited to, effects selected from the group consisting of removal of a pollutant, a reduction in odor, a reduction in chemical oxygen demand, remediation of waste, water, or soil, a degradation of a dye, a discoloration of a dye, a degradation of a lignin, degradation of paper, such as wipes (e.g., flushable and non-flushable wipes), and a combination thereof in the water, the waste, or the soil. An "effective amount" is an amount that causes any of the effects described in this paragraph.

The compositions described herein can be used to treat waste, water, or soil for any period of time that is effective to remove pollutants. For example, in one embodiment treatment of waste, water, or soil can occur daily. The time periods for treatment of waste, water, or soil are non-limiting and it should be appreciated that any time period or treatment schedule determined to be effective to remove pollutants may be used.

As used herein, for the water, waste, or soil treatment embodiments, "remove a pollutant" or "removal of a pollutant" means completely removing the pollutant, reducing the amount of the pollutant, inactivating the pollutant, degrading the pollutant, or causing the pollutant to be converted to an inactivated form, or reducing COD, reducing organics, or reducing odor in waste, and the like.

In any of the embodiments described herein, at least one of the *Bacillus* strains can have antimicrobial activity, and the antimicrobial activity can be against a bacterium selected from the group consisting of an *E. coli* bacterium, a *Salmonella* bacterium, a *Staphylococcus* bacterium, an *Enterococcus* bacterium, a *Campylobacter* bacterium, and combinations thereof.

In any of the embodiments described herein, the *Bacillus* strain can produce an enzyme selected from the group consisting of an oxidoreductase, a hydrolase, a transferase, a lyase, an isomerase, a ligase, a peroxidase, a laccase, an esterase, an amylase, a protease, a xylanase, a lipase, a cellulase, an oxygenase, a reductase, an oxidase, a hydroxylase, a dehydrogenase, and combinations thereof.

In another illustrative embodiment of the water, waste, or soil treatment methods, the pollutant can be an organic or an inorganic compound and the organic or the inorganic compound can be removed by the *Bacillus* strain by degradation of the organic or the inorganic compound by contact of the organic or the inorganic compound with the *Bacillus* strain. In yet another embodiment, the pollutant can be a synthetic compound. In still other embodiments, the pollutant can be a dye and the dye can be an azo dye or an anthraquinone dye, including but not limited to, an acid dye, a metal-complex dye, a direct dye, a basic dye, a disperse dye, a reactive dye, a sulfur dye, and/or a vat dye. In various embodiments, the azo dye can be selected from the group consisting of Reactive Red 120 (R120), Reactive Orange 16 (RO16), Direct Yellow 27 (DY27), and Reactive Black 5 (RB5). In other embodiments, the anthraquinone dye can be selected from the group consisting of Reactive Blue 4 (RB4) and Remazol Brilliant Blue R (RBBR). In another embodiment, the pollutant can be a lignin. In one aspect, the lignin can be produced by the paper industry or the pulp industry. In another embodiment, the pollutant can be paper waste, such as wipes (e.g., flushable or disposable or non-flushable wipes).

In another illustrative aspect, any antibiotics known in the art may be added to the waste, the water, or the soil along with the *Bacillus* strains described herein. In various embodiments, the antibiotic is selected from the group consisting of ampicillin, chloramphenicol, ciprofloxacin, clindamycin, tetracycline, chlortetracycline, Denagard™ (i.e., tiamulin), BMD™ (i.e., bacitracin methylene disalicylate), Carbadox™ (i.e., carbadox), Stafac™ (i.e., virginiamycin), erythromycin, levofloxacin, trimethoprim/sulfamethoxazole, trimethoprim, daptomycin, rifampicin, Tylan™ (i.e., tylosin), Pulmotil™ (i.e., tilmicosin), vancomycin, and combinations thereof. In another embodiment, antibiotics are not added to the waste, the water, or the soil with the *Bacillus* strains.

In another illustrative embodiment, one or more enzymes may be added to the waste, the water, or the soil along with the *Bacillus* strains described herein. In various embodiments, the exogenous enzymes that may be added include an exogenous enzyme selected from the group consisting of an oxidoreductase, a hydrolase, a transferase, a lyase, an isomerase, a ligase, a peroxidase, a laccase, an esterase, an amylase, a protease, a xylanase, a lipase, a cellulase, an oxygenase, a reductase, an oxidase, a hydroxylase, a dehydrogenase, and combinations thereof. In one embodiment, the enzyme added is cellulase. In another embodiment, the enzyme added is xylanase.

In various illustrative embodiments of the water, waste, or soil treatment methods, *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or a strain having all of the identifying characteristics of these strains can be added to the waste, the water, or the soil in an effective amount of about $1.0\times10^2$ CFU/gram of the water, the soil or the waste to about $1.0\times10^6$ CFU/gram of the water, the soil or the waste, in an effective amount of about $1.0\times10^2$ CFU/gram of the water, the soil or the waste to about $1.0\times10^4$ CFU/gram of the water, the soil or the waste, in an effective amount of about $1.0\times10^2$ CFU/gram of the water, the soil or the waste to about $1.0\times10^3$ CFU/gram of the water, the soil or the waste, in an effective amount of about $1.0\times10^2$ CFU/gram of the water, the soil or the waste, the water, or the soil to about $5.0\times10^{12}$ CFU/gram of the waste, the water, or the soil or at an effective amount of about $1.0\times10^2$ CFU/gram of the waste, the water, or the soil to about $1.0\times10^7$ CFU/gram of the waste, the water, or the soil. In other embodiments, the *Bacillus* strain can be added to the waste, the water, or the soil at an effective amount of greater than about $1.0\times10^2$ CFU/gram of the waste, the water, or the soil, at an effective amount of greater than about $1.0\times10^3$ CFU/gram of the waste, the water, or the soil, at an effective amount of greater than about $1.1\times10^3$ CFU/gram of the waste, the water, or the soil, at an effective amount of greater than about $1.25\times10^3$ CFU/gram of the waste, the water, or the soil, at an effective amount of greater than about $1.5\times10^3$ CFU/gram of the waste, the water, or the soil, at an effective amount of greater than about $1.75\times10^3$ CFU/gram of the waste, the water, or the soil, at an effective amount of greater than about $1.0\times10^4$ CFU/gram of the waste, the water, or the soil, at an effective amount of greater than about $2.0\times10^4$ CFU/gram of the waste, the water, or the soil, at an effective amount of greater than about $3.0\times10^4$ CFU/gram of the waste, the water, or the soil, at an effective amount of greater than about $4.0\times10^4$ CFU/gram of the waste, the water, or the soil, at an effective amount of greater than about $5.0\times10^4$ CFU/gram of the waste, the water, or the soil, at an effective amount of greater than about $6.0\times10^4$ CFU/gram of the waste, the water, or the soil, at an effective amount of greater than about $7.0\times10^4$ CFU/gram of the waste, the water, or the soil, at an effective amount of greater than about $8.0\times10^4$ CFU/gram of the waste, the water, or the soil, at an effective amount of greater than about $1.0\times10^5$ CFU/gram of the waste, the water, or the soil, at an effective amount of greater than about $1.0\times10^6$ CFU/gram of the waste, the water, or the soil, at an effective amount of greater than about $1.0\times10^7$ CFU/gram of the waste, the water, or the soil, at an effective amount of greater than about $1.0\times10^8$ CFU/gram of the waste, the water, or the soil, at an effective amount of greater than about $1.0\times10^9$ CFU/gram of the waste, the water, or the soil, at an effective amount of greater than about $1.0\times10^{10}$ CFU/gram of the waste, the water, or the soil, at an effective amount of greater than about $1.0\times10^{11}$ CFU/gram of the waste, the water, or the soil, or at an effective amount of greater than about $1.0\times10^{12}$ CFU/gram of the waste, the water, or the soil. In another embodiment, any of the amounts described herein can be in CFU/ml of water in embodiments where the strains are added to any type of wastewater to treat the wastewater.

In one aspect, these strains can be added to waste, water, or soil alone or in combination. In one embodiment, the two strains are added to waste, water, or soil in combination in a single composition. In another embodiment, the two strains are added to waste, water, or soil in combination in separate compositions.

In any embodiments described herein, the *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), or a strain having all of the identifying characteristics of these strains can be used in accordance with the methods and compositions described herein. *Bacillus* strains 1728 (NRRL No. B-67618) and 2705 (NRRL No. B-67619) were deposited on May 8, 2018 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67618 and B-67619, respectively. *Bacillus* strains *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL B-67890), and *Bacillus pumilus* MDG-1047 (NRRL No. B-67891), were deposited on Nov. 26, 2019 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67888, B-67889, B-67890, and B-67891, respectively. *Bacillus* strains *Bacillus amyloliquefaciens* MDG1607 (NRRL No. B-67666), *Bacillus subtilis* MDGV18 (NRRL No. B-67665), and *Bacillus pumilus* MDGV17 (NRRL No. B-67664) were deposited on Aug. 9, 2018 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67666, B-67665, and B-67664, respectively. The deposits were made under the provisions of the Budapest Treaty on the International Recognition of the Deposit of Microorganisms for the Purposes of patent Procedure.

As used herein "a strain having all of the identifying characteristics of" *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG-2705 (NRRL No. B-67619) can be a mutant strain having all of the identifying characteristics of *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG-2705 (NRRL No. B-67619) (e.g., having a DNA fingerprint based on DNA analysis that corresponds to the DNA fingerprint of *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG-2705 (NRRL No. B-67619), enzyme activities that correspond to *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG-2705 (NRRL No. B-67619), antimicrobial activity that corresponds to *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG-2705 (NRRL No. B-67619), antibiotic sensitivity or tolerance profiles that correspond to *Bacillus* strain *Bacillus licheniformis* MDG-1000 (NRRL No. B-67888), *Bacillus* licheniformis MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG-2705 (NRRL No. B-67619), or combinations of these identifying characteristics. In alternate embodiments, the mutation can be a natural mutation, or a genetically engineered mutation. In another embodiment, "a strain having all of the identifying characteristics of" *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG-2705 (NRRL No. B-67619), can be a strain, for example, produced by isolating one or more plasmids from *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG-2705 (NRRL No. B-67619) and introducing the one or more plasmids into another bacterium, such as another *Bacillus* strain, as long as the one or more plasmids contain DNA that provides the identifying characteristics of *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG-2705 (NRRL No. B-67619) (e.g., having a DNA fingerprint based on DNA analysis that corresponds to the DNA fingerprint of *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), or *Bacillus megaterium* MDG- 2705 (NRRL No. B-67619)). In this application, when the phrase "and strains having all of the identifying characteristics of these strains" is used in reference to a list of strains, this phrase means that the additional strains among "strains having all of the identifying characteristics of these strains" each has all of the identifying characteristics of any one strain in the list.

In an additional embodiment of the invention, compositions comprising a *Bacillus* strain selected from the group consisting of *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), and *Bacillus megaterium* MDG-2705 (NRRL No. B-67619), and combinations thereof, are provided. In one embodiment, a commercial package is provided comprising a *Bacillus* strain selected from the group consisting of *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and strains having all of the identifying characteristics of these strains, and combinations thereof.

In various embodiments, the *Bacillus* strains in the commercial package can causes an effect selected from the group consisting of removal of a pollutant, a reduction in odor, a reduction in chemical oxygen demand, a degradation of a dye, a discoloration of a dye, a degradation of a lignin, degradation of paper (e.g., a flushable or disposable or non-flushable wipes), and a combination thereof in water, waste, or soil. In another embodiment, the *Bacillus* strains can cause an effect selected from the group consisting of a degradation of a dye, a discoloration of a dye, a degradation of a lignin, and a combination thereof in water, waste, or soil. In yet another embodiment, the *Bacillus* strains can cause a discoloration of a dye or a degradation of a dye in waste, water, or soil. In still another embodiment, the *Bacillus* strains can cause a degradation of a lignin in water, waste, or soil.

In still other embodiments, the *Bacillus* strain can be administered to an animal in animal feed or in the drinking water of the animal and can improve the performance of the animal (e.g., decrease feed conversion, increase average daily feed intake, increase average daily gain, improve consistency of performance, and combinations thereof), improve the health of the animal, improve the environment of the animal, and combinations thereof.

In one illustrative aspect, in the commercial package *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains can be in the form of a concentrate (e.g., about $1\times10^8$ to about $5\times10^9$ CFU/g of the water, the waste, or the soil or the animal feed) or a super concentrate (e.g., about $1\times10^{10}$ to about $5\times10^{12}$ CFU/g of the water, the waste, or the soil or of the animal feed). In another embodiment, *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains in a composition in the commercial package, can be in a dry form (e.g., a powder or freeze-dried form), a pelleted form, a liquid form, in the form of a gel, or any other suitable form.

In another illustrative embodiment, the commercial package comprising *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains, can further comprise a carrier for the *Bacillus* strain. The carrier can be selected from the group consisting of a salt, mineral oil, a dextrin (e.g., maltodextrin), whey, sugar, sucrose, limestone, yeast culture, dried starch, sodium silico aluminate, silicon dioxide, polypropylene glycol, polysorbate 80, vegetable oil, water, rice hulls, and combinations thereof. In another embodiment, the carrier can be any suitable carrier known in the art. In another embodiment, the commercial package can contain the *Bacillus* strain in combination with any micronutrient known in the art.

In another embodiment, the commercial package comprising *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains can further comprise a binder such as clay, yeast cell wall components, aluminum silicate, glucan, or other known binders. In another embodiment, the commercial package can further comprise inorganic/organic binders, essential oils, and/or organic acids.

In yet other embodiments, the commercial package comprising *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus*

MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains can be in a container for commercial use. In various embodiments the container can be, for example, a bag (e.g., a 20-pound bag, a 50-pound bag, a 2-ounce bag, a 1-pound bag, or a 1-kilogram bag), a pouch, a drum, a bottle, or a box. In illustrative aspects, the container for the commercial package can comprise plastic, metal, foil, paper, fiber, or cardboard (e.g., a plastic pail, a paper bag, a foil bag, a fiber drum, etc.). In yet another embodiment, the commercial package can further comprise instructions for use of one or more of the *Bacillus* strains.

In any embodiments described herein for feeding the strains to animals, the *Bacillus* strains can be administered alone or in combination, and can be in the form of any suitable composition described herein. The *Bacillus* strains described herein for feeding to animals, can also be used in combination with other microbial strains, including other *Bacillus* strains or *Lactobacillus* strains.

In another embodiment, the feed additive, feed composition, or drinking water, as described herein can be administered to an animal selected from the group consisting of a poultry species, a porcine species, a caprine species, a bovine species, an ovine species, and an equine species. In another embodiment, the feed additive, feed composition, or drinking water can be administered to a human. In another aspect, the feed additive, feed composition, or drinking water, as described herein can be administered to an animal and the animal can be a porcine species and the porcine species can be selected from the group consisting of a grow finish pig, a nursery pig, a sow, and a breeding stock pig. In yet another embodiment, the feed additive, feed composition, or drinking water can be administered to an animal selected from the group consisting of a chicken, a pig, a horse, a pony, a cow, a turkey, a goat, a sheep, a quail, a pheasant, an ostrich, a duck, a fish, a crustacean, and combinations thereof.

In one embodiment for feeding to animals, an effective amount of the *Bacillus* strain can be administered to the animal to improve performance, health, or the environment of the animal. By "effective amount" is meant an amount of the *Bacillus* strain capable of improving performance, health, or the environment of the animal, by any mechanism.

In embodiments described herein wherein the compositions of the present invention comprising *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains are administered to an animal, the compositions are preferably administered to animals orally in a feed composition or in drinking water, but any other effective method of administration known to those skilled in the art may be utilized such as in a paste, a liquid drench, a top dress, or a capsule. In one illustrative embodiment, *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains are provided in the form of an additive for addition to the drinking water of an animal.

In another illustrative embodiment, *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains are provided in the form of a feed additive for addition to a feed composition. The feed composition may contain *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these in a mixture with an animal feed blend, including any art-recognized animal feed blend or any animal feed blend described herein. As used herein, "feed composition" or "animal feed composition" means a feed composition comprising *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains in a mixture with an animal feed blend, and, optionally any other components that could be used in a feed composition, including other bacterial strains, such as other *Bacillus* strains or *Lactobacillus* strains. In one embodiment, the feed composition may be in the form of a ground meal.

Any animal feed blend, including those known in the art and those described herein, may be used in accordance with the methods described in this patent application, such as rapeseed meal, cottonseed meal, soybean meal, cornmeal, barley, wheat, silage, and haylage. In various embodiments, the animal feed blend can be supplemented with *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No.

B-67618), *Bacillus megaterium* MDG-2705 (NRRL No. B-67619), and/or strains having all of the identifying characteristics of these strains, but other ingredients may optionally be added to the animal feed blend, including other bacterial strains, such as other *Bacillus* strains or *Lactobacillus* strains.

In various illustrative embodiments, optional ingredients of the animal feed blend include sugars and complex carbohydrates such as both water-soluble and water-insoluble monosaccharides, disaccharides, and polysaccharides. Other optional ingredients include dried distillers grain solubles, fat (e.g., crude fat), phosphorous, sodium bicarbonate, limestone, salt, phytate, calcium, sodium, sulfur, magnesium, potassium, copper, iron, manganese, zinc, ash, fish oil, an oil derived from fish meal, raw seed (e.g., flaxseed), an antioxidant, and starch. In another embodiment, minerals may be added in the form of a mineral premix.

Optional amino acid ingredients that may be added to the animal feed blend are arginine, histidine, isoleucine, leucine, lysine, cysteine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that may be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. In another embodiment, vitamins may be added in the form of a vitamin premix. In yet another embodiment, protein ingredients may be added to the animal feed blend and include protein obtained from meat meal, bone meal, or fish meal, liquid or powdered egg, fish solubles, crude protein, and the like.

In various embodiments, antibiotics can be added along with the *Bacillus* strains to the animal feed compositions or to the drinking water of the animal for use in the methods of feeding animals described herein and are selected from the group consisting of ampicillin, chloramphenicol, ciprofloxacin, clindamycin, tetracycline, chlortetracycline, Denagard™ (i.e., tiamulin), BMD™ (i.e., bacitracin methylene disalicylate), Carbadox™ (i.e., carbadox), Stafac™ (i.e., virginiamycin), erythromycin, levofloxacin, trimethoprim/sulfamethoxazole, trimethoprim, daptomycin, rifampicin, Tylan™ (i.e., tylosin), Pulmotil™ (i.e., tilmicosin), vancomycin, avilamycin (Kavault™), gentamycin, and neomycin, and combinations thereof. In one illustrative embodiment, the antibiotic is selected from the group consisting of tylosin, tilmicosin, avilamycin, gentamycin, and neomycin.

In another illustrative embodiment, one or more enzymes may be added to the animal feed blend. In various embodiments, the enzymes that may be added include a galactosidase, a phytase, a protease, a lipase, an amylase, a hemicellulase, an arabinoxylanases, a xylanase, a cellulase, an NSPase, combinations thereof, and any other enzyme that improves the effectiveness of the feed composition for improving the health, the performance, or the environment of the animal. In yet another embodiment, yeast, fungi (e.g., *Aspergillus* or *Trichoderma*), or micronutrients may be added to the animal feed. Any of the ingredients described above that are suitable for addition to an additive for the drinking water of the animal may be added as a component of the additive for the drinking water of the animal as described herein.

In various illustrative embodiments, the *Bacillus* strain (e.g., *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains), or any other bacterial strains added in addition to *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains can be administered in the feed composition at a dose of about $1.0 \times 10^3$ CFU/gram of the feed composition to about $5.0 \times 10^{12}$ CFU/gram of the feed composition or at a dose of about $1.0 \times 10^3$ CFU/gram of the feed composition to about $1.0 \times 10^7$ CFU/gram of the feed composition. In other embodiments, the *Bacillus* strain (e.g., *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains) is administered in the feed composition at a dose greater than about $1.0 \times 10^3$ CFU/gram of the feed composition, at a dose greater than about $1.1 \times 10^3$ CFU/gram of the feed composition, at a dose greater than about $1.25 \times 10^3$ CFU/gram of the feed composition, at a dose greater than about $1.5 \times 10^3$ CFU/gram of the feed composition, at a dose greater than about $1.75 \times 10^3$ CFU/gram of the feed composition, at a dose greater than about $1.0 \times 10^4$ CFU/gram of the feed composition, at a dose greater than about $2.0 \times 10^4$ CFU/gram of the feed composition, at a dose greater than about $3.0 \times 10^4$ CFU/gram of the feed composition, at a dose greater than about $4.0 \times 10^4$ CFU/gram of the feed composition, at a dose greater than about $5.0 \times 10^4$ CFU/gram of the feed composition, at a dose greater than about $6.0 \times 10^4$ CFU/gram of the feed composition, at a dose greater than about $7.0 \times 10^4$ CFU/gram of the feed composition, at a dose greater than about $8.0 \times 10^4$ CFU/gram of the feed composition, at a dose greater than about $1.0 \times 10^5$ CFU/gram of the feed composition, at a dose greater than about $1.0 \times 10^6$ CFU/gram of the feed composition, at a dose greater than about $1.0 \times 10^7$ CFU/gram of the feed composition, at a dose greater than about $1.0 \times 10^8$ CFU/gram of the feed composition, at a dose greater than about $1.0 \times 10^9$ CFU/gram of the feed composition, at a dose greater than about $1.0 \times 10^{10}$ CFU/gram of the feed composition, at a dose greater than about $1.0 \times 10^{11}$ CFU/gram of the feed composition, or at a dose greater than about $1.0 \times 10^{12}$ CFU/gram of the feed composition. In another embodiment, the *Bacillus* strain (e.g., *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacil-* lus subtilis MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains), or any other bacterial strains added in addition to *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains, can be administered in the feed composition at a dose of about $1.0 \times 10^2$ CFU/gram of the feed composition to about $5.0 \times 10^{12}$ CFU/gram of the feed composition or at a dose of about $1.0 \times 10^2$ CFU/gram of the feed composition to about $1.0 \times 10^7$ CFU/gram of the feed composition, or at a dose greater than about $1.0 \times 10^2$ CFU/gram of the feed composition. In another embodiment, any of the dosages described herein can be in CFU/ml of drinking water in embodiments where the strains are administered in the drinking water of the animal.

The feed composition or drinking water comprising *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains, may be administered to the animal for any time period that is effective to improve the health or the performance of the animal. For example, in one embodiment the feed composition or drinking water may be provided to the animal daily. In an alternate embodiment, the feed composition or drinking water may be administered to the animal during lactation and/or during gestation. The time periods for administration of the feed composition or drinking water described above are non-limiting examples and it should be appreciated that any time period or administration schedule determined to be effective to improve the health or the performance of the animal, may be used.

In one embodiment, the feed additive for addition to an animal feed blend to produce a complete feed composition can be mixed with the animal feed blend, for example, with an automated micro-nutrient delivery system, or, for example, by hand-weighing and addition to achieve any of the doses of *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains, described herein, for administration to the animal in the form of a complete feed composition. The mixing can also be done by any other suitable method known in the art for combining direct-fed microbials with an animal feed blend to obtain a uniform mixture. In various embodiments, the mixing can be done for any suitable time period (e.g., about 1 to about 4 minutes). In the embodiment where *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains, are in the form of an additive for the drinking water of the animal, the *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains, can be in the form of, for example, a powder, a liquid, or pellets, and can be mixed with the drinking water using any suitable method known in the art to achieve any of the doses of *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains, described herein, for administration to the animal in the drinking water of the animal. *Bacillus* strain *Bacillus licheniformis* MDG-1000 (NRRL No. B-67888), *Bacillus licheniformis* MDG-1001 (NRRL No. B-67889), *Bacillus subtilis/amyloliquefaciens* MDG-8001 (NRRL No. B-67890), *Bacillus pumilus* MDG-1047 (NRRL No. B-67891), *Bacillus amyloliquefaciens* MDG1607 (NRRL No. B-67666), *Bacillus subtilis* MDGV18 (NRRL No. B-67665), *Bacillus pumilus* MDGV17 (NRRL No. B-67664), *Bacillus subtilis* MDG-1728 (NRRL No. B-67618), *Bacillus megaterium* MDG-2705 (NRRL No. B-67619), and/or strains having all of the identifying characteristics of these strains, can also be fed directly to the animal orally (i.e., by oral insertion) in the form of a powder, a liquid, or a pellet.

In one illustrative aspect, the strains for addition to the feed additive, additive for the drinking water of the animal, or the feed composition can be in the form of a concentrate (e.g., about $1 \times 10^8$ to about $5 \times 10^9$ CFU/g) or a super concentrate (e.g., about $1 \times 10^{10}$ to about $5 \times 10^{12}$ CFU/g). In another embodiment, the strains for addition to the feed additive, feed composition, or additive for the drinking water of the animal can be in a dry form (e.g., a powder), a pelleted form, a liquid form, in the form of a top-dressing, or in the form of a gel, or any other suitable form.

In another illustrative embodiment, the feed additive, the additive for the drinking water of the animal, or the feed composition can further comprise a carrier for the *Bacillus* strain. The carrier can be selected from the group consisting of a bran, rice hulls, a salt, mineral oil, a dextrin (e.g., maltodextrin), water, whey, sugar, sucrose, limestone, yeast culture, dried starch, sodium silico aluminate, silicon dioxide, polypropylene glycol, polysorbate 80, vegetable oil, and combinations thereof. In another embodiment, the carrier can be any suitable carrier known in the art for a direct-fed microbial. In another embodiment, the feed additive, the additive for the drinking water of the animal, or the feed composition can further comprise a binder such as clay, yeast cell wall components, aluminum silicate, glucan, or other known binders. In another embodiment, the commercial package, the feed additive, the additive for the drinking water of the animal, or the feed composition can further comprise inorganic/organic binders, essential oils, and/or organic acids.

The following EXAMPLES provide various additional illustrative aspects of the invention described herein and are not intended to be limiting in any way.

EXAMPLES

Example 1

Bioremediation of Colorants from Mineral Media

Lab-scale testing was conducted for triplicate experiments in mineral media with six separate colorants from Millipore Sigma: Reactive Red 120 (R120); Reactive Orange 16 (RO16); Direct Yellow 27 (DY27); Reactive Blue 4 (RB4); Reactive Black 5 (RB5); and Remazol Brilliant Blue R (RBBR). Dye stocks for each colorant were made by mixing dye with deionized water at 0.05%. Stocks were centrifuged and the upper phase was decanted to new tubes. Dye stocks were added to six jars of mineral medium at the following concentrations: 0.05% (w/v), 0.05% (w/v), 0.09% (w/v), 0.05% (w/v), 0.05% (w/v), and 0.05% (w/v), respectively, and sterilized at 121° C. for 30 minutes. Three preparations were made—a Control containing sterile mineral medium; Treatment-1 (TRT-1) including the mineral medium and MDG-1728; and Treatment-2 (TRT-2) including mineral medium and MDG-2705. The initial experiment was conducted in duplicate and the following were in quadruplicate. Inoculation for each of the six media varieties occurred following growth of microorganisms in flasks with mineral medium (no colorant) incubated for 72 hours, at 30° C., 150 rpm (pH=7.0). Optical density (OD) was read at 600 nm for each preparation; Control absorbance was used to blank the spectrophotometer at 0.00 nm, MDG-1728 OD=1.73 nm, and MDG-2705 OD=1.69 nm. Preparations were added to six varieties of dye media including one of the following colorants: R120, R016, DY27, RB4, RB5 or RBBR. Samples were incubated for 24 hours, at 30° C., 150 rpm.

Post incubation, samples were analyzed spectrophotometrically at the λmax for each colorant using Controls as blanks. Negative absorbance in nanometers (nm) of treated samples indicated decolorization. Statistical significance of treatment was determined using one-way analysis of variance (ANOVA) for the ten combined replicates for each media variety and treatment. Treatment-1 significantly reduced the absorbance of all dye media (p<0.01); Treatment-2 significantly reduced the absorbance of all dye media (p<0.01) with the exception of DY27.

Example 2

Results and Analysis from Bioremediation of Colorants from Mineral Media

Results and analyses include outliers for each preparation (combined n=10). Controls were used to blank the spectrophotometer at the maximum wavelength (λmax) for each colorant; absorbance was measured for each treated preparation. All treated samples show statistical significance following one-way ANOVA with p-values <0.01; this excludes DY27 media with Treatment-2 where the p-value was insignificant (Table 1). The decrease in absorbance for each colorant and Treatment-1 (TRT-1) are as follows: R120=−0.28±0.05; RO16=−0.18±0.04; DY27=−0.05±0.04; RB4=−0.02±0.01; RB5=−0.10±0.03; and RBBR=−0.04±0.003. The decrease in absorbance for each colorant and Treatment-2 (TRT-2) are as follows: R120=−0.33±0.08; RO16=−0.31±0.08; DY27=−0.002±0.03; RB4=−0.02±0.004; RB5=−0.14±0.006; and RBBR=−0.02±0.006. Results are graphed in FIGS. 1A-1F; error bars represent the standard error of the mean. The average pH following incubation for all samples was pH=7.02±0.28.

TABLE 1

Results from bioremediation of colorants from mineral media.

| DYE | λ MAX | TRT-1 AVG | TRT-1 SEM | TRT-1 P-VAL | TRT-2 AVG | TRT-2 SEM | TRT-2 P-VAL | pH AVG |
|---|---|---|---|---|---|---|---|---|
| R120 | 510 nm | −0.2791 | 0.0165 | <0.01 | −0.3268 | 0.0259 | <0.01 | 7.07 |
| RO16 | 493 nm | −0.1795 | 0.0130 | <0.01 | −0.3077 | 0.0241 | <0.01 | 7.00 |
| DY27 | 393 nm | −0.0469 | 0.0122 | <0.01 | −0.0015 | 0.0105 | >0.05 | 6.99 |
| RB4 | 595 nm | −0.0224 | 0.0018 | <0.01 | −0.0159 | 0.0012 | <0.01 | 7.00 |
| RB5 | 597 nm | −0.0969 | 0.0080 | <0.01 | −0.1355 | 0.0020 | <0.01 | 7.03 |
| RBBR | 595 nm | −0.0417 | 0.0010 | <0.01 | −0.0233 | 0.0018 | <0.01 | 7.04 |

Example 3

Analysis of Lignin Peroxidase

Lab-scale testing was conducted to confirm quantitative lignin peroxidase production from MDG-1728 and MDG-2705 using 10-Acetyl-3,7 dihydroxyphenoxazine which, in the presence of peroxidase and excess hydrogen peroxide ($H_2O_2$), produces the fluorescent intermediate resorufin, which can be used to measure enzyme activity.

All reagents and inoculants were prepared prior to the experiment. MDG-1728 and MDG-2705 were grown in separate flasks in mineral medium+TSB, incubated for 72 hours, at 30° C., 150 rpm (pH=7.0). Culture was centrifuged, the upper phase decanted to Pierce Protein Concentrator tubes (PES, 100k MWCO, 5-20 mL). Concentrator tubes were centrifuged at 4000 rpm for 15 minutes, the supernatants was used as inoculants following harvest. The positive control consisted of 0.5 U/mL lignin peroxidase in 50 mM cold phosphate buffer (0.1 μm filter-sterile, pH 7.4); cooled to −20° C. A 10-Acetyl-3,7 dihydroxyphenoxazine stock solution was prepared under light-limitation with 2.5 ppm Ampliflu™ Red in dimethyl sulfoxide. A 0.50% w/w Hydrogen peroxide solution was prepared using molecular water; 0.1p m filter-sterilized, cooled to −4° C.

Two working solutions were prepared under ambient light by adding 60 μl 10-Acetyl-3,7 dihydroxyphenoxazine stock to 12 mL sterile molecular water, split into 6 mL aliquots. 1 mL sterile molecular water was added to one and 1 mL 0.50% w/w Hydrogen peroxide solution to the other. 180 μl for each working stock was added to a 96-well plate, 32 wells each. Four preparations were made; the Negative Control had 20 μl sterile mineral medium+TSB pipetted to 8 of the 32 replicates for each working solution (−Control/Blank), the Positive Control had 20 μl lignin peroxidase solution pipetted to 8 of the 32 replicates for each working solution, Treatment-1 (TRT-1) had 20 μl MDG-1728 supernatant pipetted to 8 of the 32 replicates for each working solution, and Treatment-2 (TRT-2) had 20 μl MDG-2705 supernatant pipetted to 8 of the 32 replicates for each working solution. The plate was read using a Multiskan™ GO Microplate Spectrophotometer at λ=570 nm following 30 minutes incubation at room temperature under light limitation.

Example 4

Results and Analysis of Lignin Peroxidase

Lignin peroxidase can be measured by catalyzing the reaction of $H_2O_2$ and 10-Acetyl-3,7-dihydroxyphenoxazine at 1:1 stoichiometric ratios. This reagent is used as a colorimetric/fluorometric indicator acting as an electron donor during the reduction of $H_2O_2$ to water in the presence of peroxidase, producing fluorescent intermediate resorufin. Results from this experiment show quantitative peroxidase production in the Positive Control, MDG-1728 and MDG-2705. Fluorescing of the negative controls is indicative of photo-oxidation-. Preparations in working solutions without $H_2O_2$ should have minimal to no reaction. Outliers were determined using the Iglewicz and Hoaglin outlier test (1993), "Volume 16: How to Detect and Handle Outliers", the ASQC Basic References in Quality Control: Statistical Techniques, Edward F. Mykytka, Ph.D., Editor. Average percent difference in absorbance between negative Control sample averages with $H_2O_2$ and Positive Control sample averages with $H_2O_2$ showed an increase at 0.01825 nm (17%), TRT-1 with $H_2O_2$ showed an increase at 0.04482 nm (42%), and TRT-2 with $H_2O_2$ showed an increase at 0.0273 nm (26%).

Example 5

Degradation of Flushable Wet Wipes

The degradation of flushable wet wipes was evaluated in an in vitro experiment. A popular brand of nonwoven flushable wet wipes was chosen for this test. Individual wipes were allowed to air dry and the dry weight was recorded. One wipe was placed in a 250 ml Erlenmeyer flask with 200 ml of a low nutrient mineral media to simulate a wastewater environment. Flasks were inoculated with 1.00 E+06 cfu/ml of *Bacillus* and 5 U/ml of cellulase, or sterile water in the control flasks. The flasks were placed in a shaking incubator at 25° C. and 190 rpm for 3 or 7 days. At the end of the incubation period the contents of the flask were poured through a 2 mm sieve. The remaining materials were placed in an incubator to dry. The dry weights were recorded and compared to initial weights to calculate the percent loss in dry weight. Difference in means was evaluated using a two sample t test.

Figure 2:
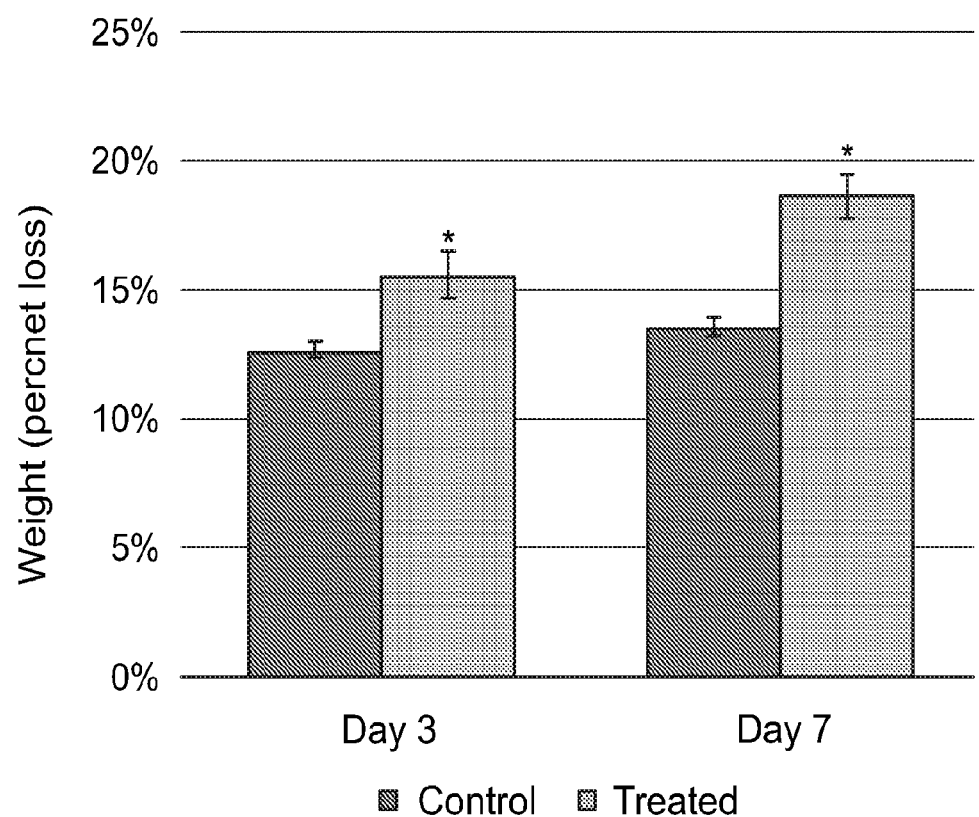
FIG. 2 shows degradation of wet wipes treated with *Bacillus* and cellulase for 3 and 7 days, in percent loss of dry weight. The asterisk (*) indicates the value is significantly different from the control ($p<0.05$).
Figure 3A:
FIG. 3A to D show wet wipes after 7 days in a shaking incubator in an untreated flask (FIG. 3A), an untreated wipe after draining through 2 mm sieve (FIG. 3B), a *Bacillus* and cellulase treated wipe in a flask (FIG. 3C), and a *Bacillus* and cellulase treated wipe after draining through a 2 mm sieve (FIG. 3D).
Figure 3B:
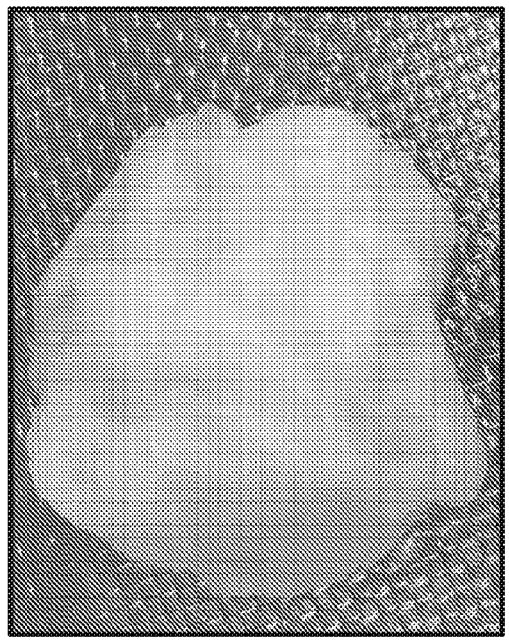
Figure 3C:
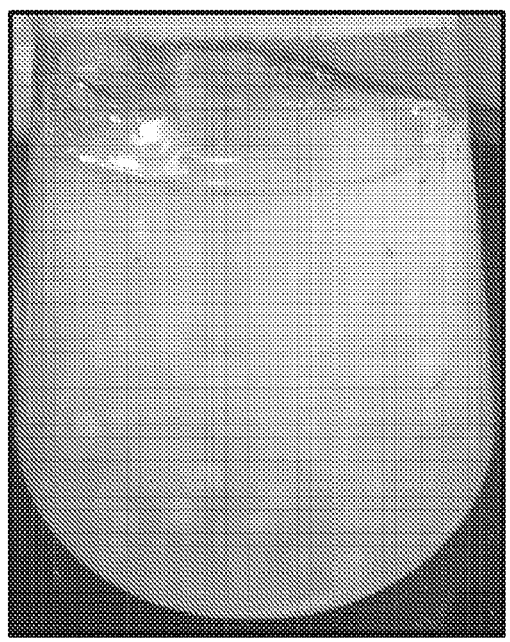
Figure 3D:
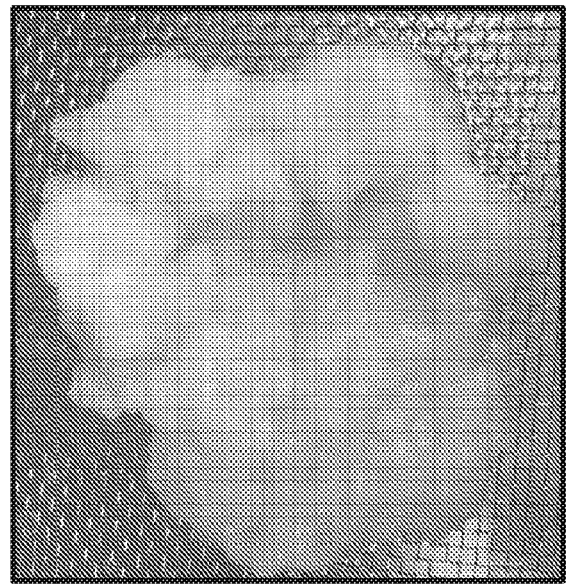
Figure 4:
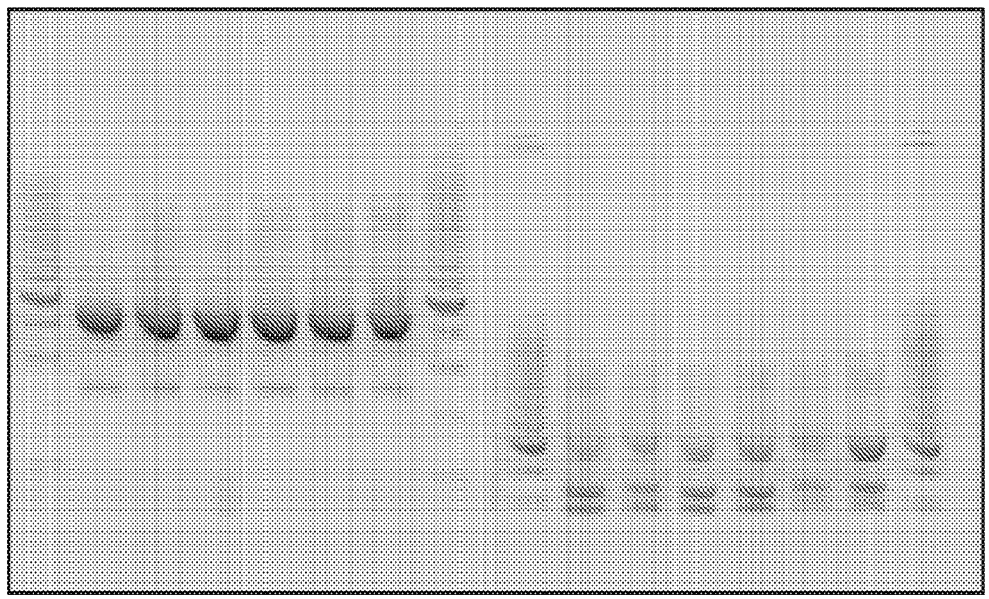
FIG. 4 shows a photograph of a gel displaying RAPD-PCR profiles for *Bacillus* strain 1000. The leftmost and rightmost lanes, for each group of eight lanes, include markers.
Figure 5:
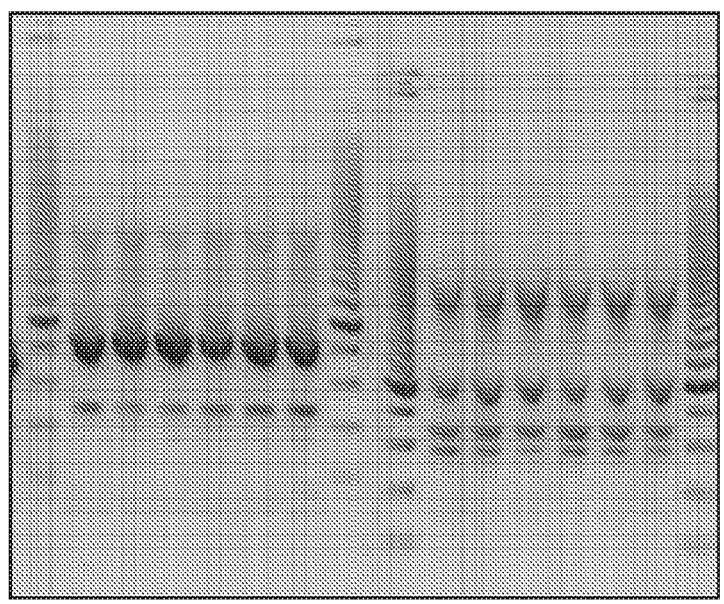
FIG. 5 shows a photograph of a gel displaying RAPD-PCR profiles for *Bacillus* strain 1001. The leftmost and rightmost lanes, for each group of eight lanes, include markers.
Figure 6:
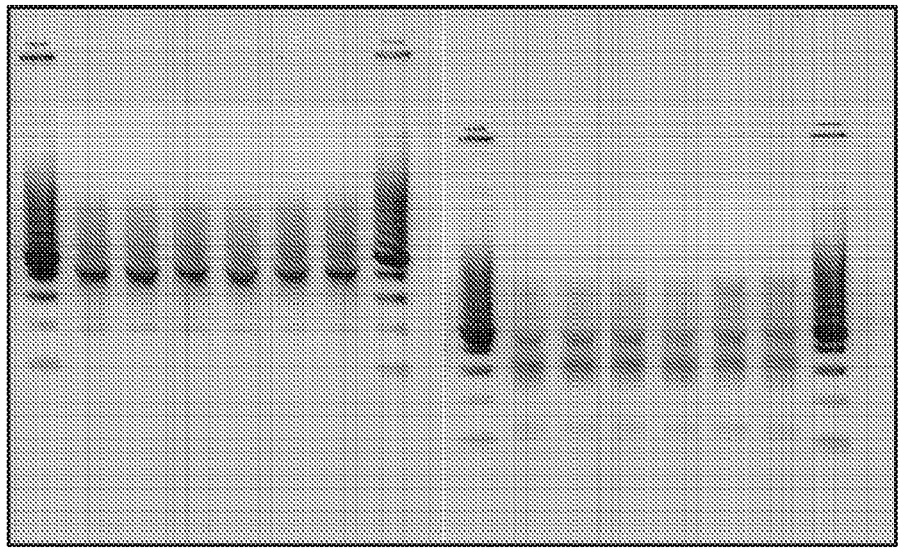
FIG. 6 shows a photograph of a gel displaying RAPD-PCR profiles for *Bacillus* strain 8001. The leftmost and rightmost lanes, for each group of eight lanes, include markers.
Figure 7:
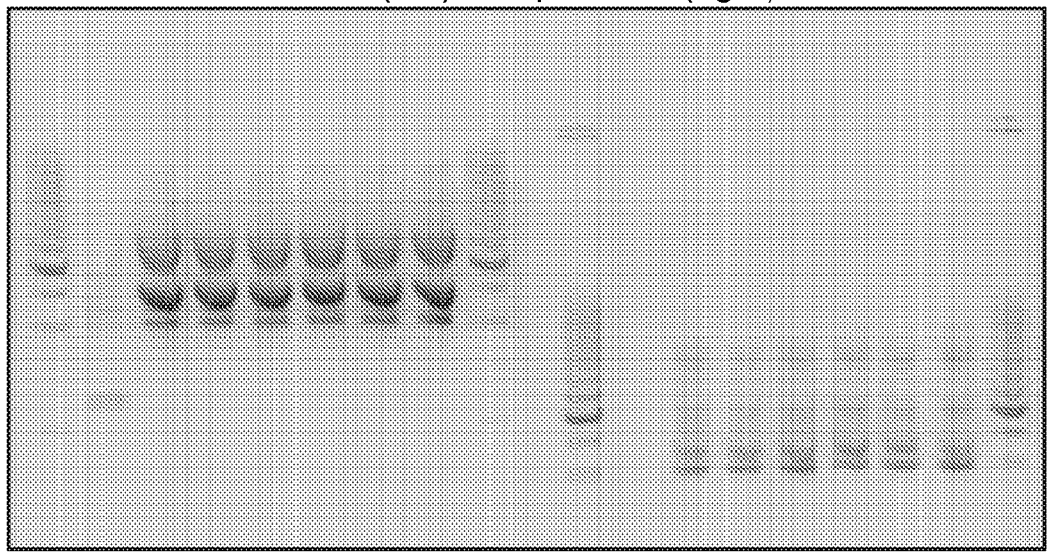
FIG. 7 shows a photograph of a gel displaying RAPD-PCR profiles for *Bacillus* strain 1047. The leftmost and rightmost lanes, for each group of eight lanes, include markers.
Figure 8:
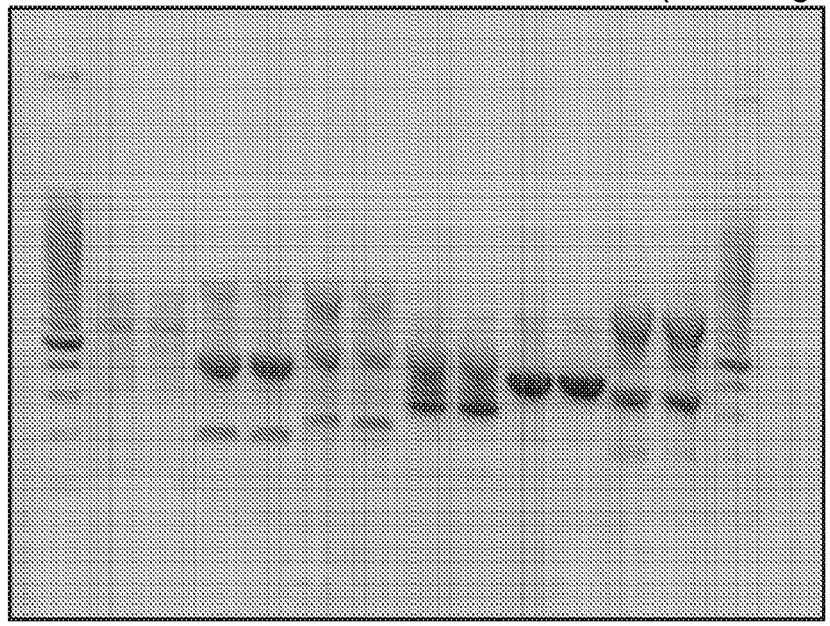
FIG. 8 shows a photograph of a gel displaying RAPD-PCR profiles for *Bacillus* strain 1607. The leftmost and rightmost lanes include markers.
Figure 9:
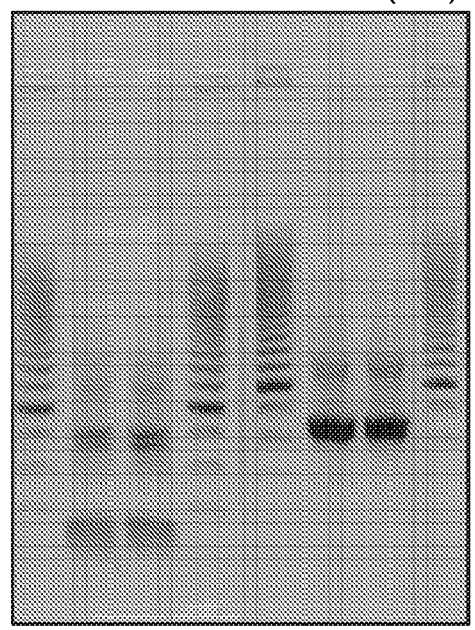
FIG. 9 shows a photograph of a gel displaying RAPD-PCR profiles for *Bacillus* strain V18. The leftmost and rightmost lanes, for each group of four lanes, include markers.
Figure 10:
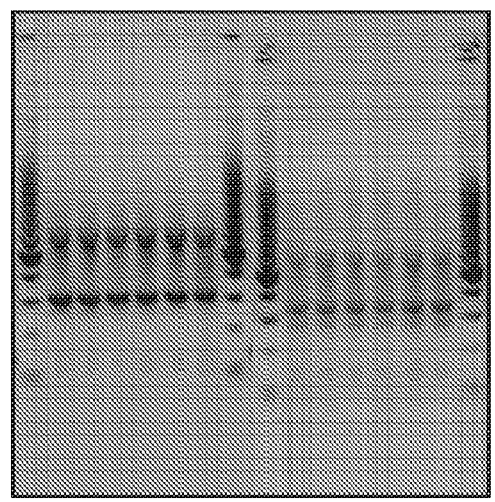
FIG. 10 shows a photograph of a gel displaying RAPD-PCR profiles for *Bacillus* strain V17. The leftmost and rightmost lanes, for each group of eight lanes, include markers.
Figure 11:
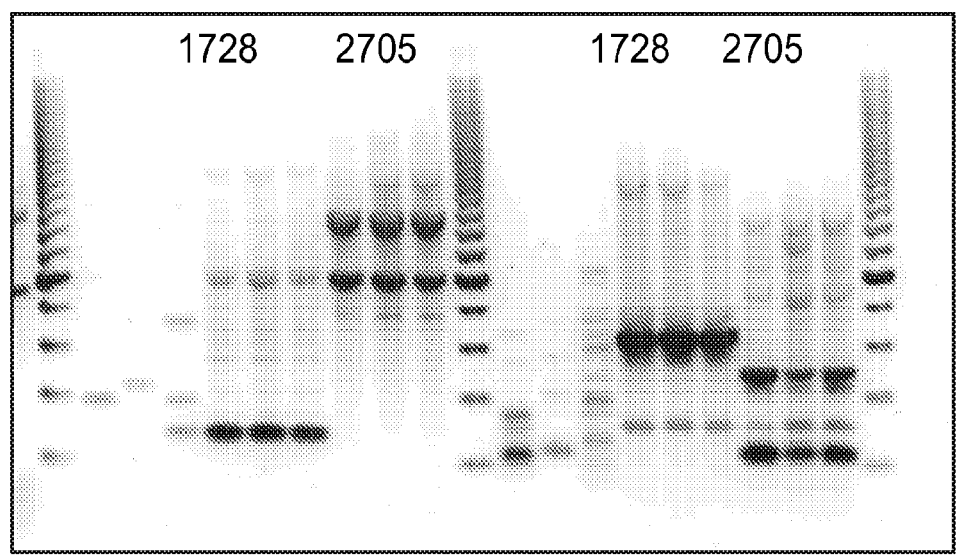
FIG. 11 shows a photograph of a gel displaying RAPD-PCR profiles for *Bacillus* strains 1728 and 2705. The leftmost and rightmost lanes, and the middle lane, include markers.

After 3 days and 7 days treatment, there was a significant increase ($p<0.05$) in the degradation of wet wipes treated with *Bacillus* and cellulase compared to control (FIG. 2). The loss in dry weight after 3 days increased from an average of 12.6% in the control group to 15.5% in the treated group. After 7 days the loss in dry weight increased from 13.5% in the control group to 18.6% in the control group. In addition to the loss in weight, the structure of the wipe appeared changed in treated flasks (FIG. 3). The untreated wipe retained the appearance and structure of a wipe, while the treated wipe broke down into small pieces that formed a spherical shape due to the flask rotation.

Example 6

Enzyme Production by *Bacillus* Species

*Bacillus* strains were tested for their ability to produce cellulase and xylanase, enzymes that aid in the degradation of cellulose and xylan, common components of wood pulp and paper. *Bacillus* strains were grown in tryptic soy broth ay 37° C. overnight, then 2 μl of culture was spotted on tryptic soy agar plates supplemented with either 0.5% carboxymethylcellulose (CMC) or 1% xylan. The agar plates were incubated for 24 hours at 37° C. The CMC plates were stained with iodine for 1 minute. The presence of an unstained zone around the *Bacillus* colonies indicated cellulase activity. A zone of clearing around *Bacillus* colonies on the xylan plates indicated the presence of xylanase activity.

TABLE 2

Presence (+) or absence (−) of cellulase and xylanase activity in *Bacillus* strains.

| Strain | Cellulase | Xylanase |
| --- | --- | --- |
| MDG-1728 | − | + |
| MDG-2705 | + | + |
| MDG-1000 | + | + |
| MDG-1001 | + | + |
| MDG-8001 | − | + |
| MDG1607 | + | + |
| MDG-1047 | + | + |
| MDGV18 | + | + |

Example 7

RAPD-PCR DNA Profiles

The Randomly Amplified Polymorphic DNA PCR method (herein referred to as RAPD-PCR) was used to identify genetic variability of each strain. Preparation of the DNA to be used in the RAPD-PCR reaction was done by using the QIAGEN® Tissue and Blood single column kit (QIAGEN®, Venlo, The Netherlands). FIGS. 4 to 11 illustrate RAPD-PCR results for the strains described in this application. The results show that the strains are unique from each other.

What is claimed is:

1. A method of treating water, soil or waste by contacting the water, the soil or the waste with a *Bacillus* strain to remove a pollutant, the method comprising contacting the water, the soil or the waste with a composition comprising an effective amount of isolated *Bacillus* strains that express both cellulase and xylanase activity, said *Bacillus* strains comprising *Bacillus megaterium* MDG-2705, deposited as accession number NRRL No. B-67619, *Bacillus licheniformis* MDG-1000, deposited as accession number NRRL No. B-67888, and *Bacillus licheniformis* MDG-1001, deposited as accession number NRRL No. B-67889, wherein the *Bacillus* strains are in the form of a powder, a freeze-dried composition, a gel, or a pellet.

2. The method of claim 1 wherein the water or the waste is treated to remove a pollutant and the water or the waste is selected from the group consisting of industrial wastewater, industrial waste, residential wastewater, residential waste, agricultural wastewater, agricultural waste, and wastewater.

3. The method of claim 1 wherein removing the pollutant results in a reduction in odor or a reduction in chemical oxygen demand in the water, the waste, or the soil.

4. The method of claim 1 wherein the pollutant is an organic compound.

5. The method of claim 4 wherein the organic compound is removed by degradation.

6. The method of claim 1 wherein the pollutant is a synthetic compound.

7. The method of claim 1 wherein the pollutant is a paper-containing compound.

8. The method of claim 7 wherein the paper-containing compound is a wipe.

9. The method of claim 1 wherein the *Bacillus* strain produces an enzyme selected from the group consisting of an oxidoreductase, a hydrolase, a transferase, a lyase, an isomerase, a ligase, a peroxidase, a laccase, an esterase, an amylase, a protease, a xylanase, a lipase, a cellulase, an oxygenase, a reductase, an oxidase, a hydroxylase, a dehydrogenase, and combinations thereof.

10. The method of claim 1 further comprising contacting the water, the soil, or the waste with an exogenous enzyme selected from the group consisting of an oxidoreductase, a hydrolase, a transferase, a lyase, an isomerase, a ligase, a peroxidase, a laccase, an esterase, an amylase, a protease, a xylanase, a lipase, a cellulase, an oxygenase, a reductase, an oxidase, a hydroxylase, a dehydrogenase, and combinations thereof.

11. The method of claim 1 wherein the pollutant is a dye.

12. The method of claim 11 wherein the dye is an azo dye or an anthraquinone dye.

13. The method of claim 1 wherein said composition further comprises one or more *Bacillus* strains selected from the group consisting of *Bacillus pumilus* MDG-1047, deposited as accession number NRRL No. B-67891, *Bacillus amyloliquefaciens* MDG1607, deposited as accession number NRRL No. B-67666, *Bacillus subtilis* MDGV18, deposited as accession number NRRL No. B-67665, *Bacillus pumilus* MDGV17, deposited as accession number NRRL No. B-67664, *Bacillus subtilis/amyloliquefaciens* MDG-8001, deposited as accession number NRRL No. B-67890, and *Bacillus subtilis* strain MDG-1728, deposited as accession number NRRL No. B-67618.

14. The method of claim 11 wherein the pollutant is a sulfur dye.

15. The method of claim 1 wherein the pollutant is a dye and the *Bacillus* strain causes degradation or discoloration of the dye.

16. The method of claim 1 wherein the pollutant is a lignin.

17. The method of claim 16 wherein the lignin is produced by the paper industry or the pulp industry.

18. The method of claim 1 wherein the pollutant is an inorganic compound.

19. A commercial package comprising isolated *Bacillus* strains that express both cellulase and xylanase activity, said *Bacillus* strains comprising *Bacillus megaterium* MDG-2705, deposited as accession number NRRL No. B-67619, *Bacillus licheniformis* MDG-1000, deposited as accession number NRRL No. B-67888, and *Bacillus licheniformis* MDG-1001, deposited as accession number NRRL No. B-67889, wherein the *Bacillus* strains are in the form of a powder, a freeze-dried composition, a gel, or a pellet.

20. The commercial package of claim 19 wherein said package further comprises one or more *Bacillus* strains selected from the group consisting of *Bacillus pumilus* MDG-1047, deposited as accession number NRRL No. B-67891, *Bacillus amyloliquefaciens* MDG1607, deposited as accession number NRRL No. B-67666, *Bacillus subtilis* MDGV18, deposited as accession number NRRL No. B-67665, *Bacillus pumilus* MDGV17, deposited as accession number NRRL No. B-67664, *Bacillus subtilis/amyloliquefaciens* MDG-8001, deposited as accession number NRRL No. B-67890, and *Bacillus subtilis* MDG-1728, deposited as accession number NRRL No. B-67618.

21. The commercial package of claim 20 wherein said one or more *Bacillus* strains comprise *Bacillus subtilis* MDG-1728, deposited as accession number NRRL No. B-67618.

22. The commercial package of claim 19 further comprising a binder.

23. The commercial package of claim 22 wherein the binder is selected from the group consisting of clay, yeast cell wall components, aluminum silicate, glucan, and combinations thereof.

24. The commercial package of claim 19 further comprising a cellulase.

25. The commercial package of claim 19 wherein said commercial package further comprises one or more *Bacillus* strains selected from the group consisting of *Bacillus pumilus* MDG-1047, deposited as accession number NRRL No. B-67891 and *Bacillus subtilis* MDG-1728, deposited as accession number NRRL No. B-67618.

* * * * *